US012727882B2

(12) United States Patent
Fanelli et al.

(10) Patent No.: US 12,727,882 B2
(45) Date of Patent: Sep. 8, 2026

(54) SURGICAL STAPLER CARTRIDGE HAVING TISSUE ENGAGEMENT PROTRUSIONS WITH ENLARGED ENGAGEMENT SURFACE

(71) Applicant: Cilag GmbH International, Zug (CH)

(72) Inventors: Nicholas Fanelli, Morrow, OH (US); Gregory G. Scott, Cincinnati, OH (US); Kevin M. Fiebig, Cincinnati, OH (US); Scott A Jenkins, Mason, OH (US)

(73) Assignee: Cilag GmbH International, Zug (CH)

( * ) Notice: Subject to any disclaimer, the term of this patent is extended or adjusted under 35 U.S.C. 154(b) by 100 days.

(21) Appl. No.: 18/588,175

(22) Filed: Feb. 27, 2024

(65) Prior Publication Data

US 2024/0382196 A1 Nov. 21, 2024

Related U.S. Application Data

(60) Provisional application No. 63/467,623, filed on May 19, 2023.

(51) Int. Cl.
*A61B 17/068* (2006.01)
*A61B 17/072* (2006.01)

(52) U.S. Cl.
CPC ........ *A61B 17/0686* (2013.01); *A61B 17/072* (2013.01); *A61B 2017/07271* (2013.01)

(58) Field of Classification Search
CPC .............. A61B 17/0686; A61B 17/072; A61B 2017/07271; A61B 17/07207; A61B 17/07292

(Continued)

(56) References Cited

U.S. PATENT DOCUMENTS 8,453,914 B2 6/2013 Laurent et al.
9,186,142 B2 11/2015 Fanelli et al.
(Continued)

FOREIGN PATENT DOCUMENTS

EP 2932914 A1 10/2015
EP 3348209 A2 * 7/2018 ....... A61B 17/07207
(Continued)

OTHER PUBLICATIONS

U.S. Appl. No. 18/588,094, entitled "Incompatible Staple Cartridge Use Prevention Features for Surgical Stapler,", filed Feb. 27, 2024.
(Continued)

*Primary Examiner* — Linda J. Hodge
(74) *Attorney, Agent, or Firm* — FBT Gibbons LLP

(57) ABSTRACT

An apparatus includes a cartridge body, a deck, an elongate slot, a plurality of pockets, and a plurality of engagement protrusions. The plurality of engagement protrusions extend from the deck and are configured to grip tissue or an adjunct material. The plurality of engagement protrusions include a first engagement protrusion associated with the first pocket. The first engagement protrusion includes a first inwardly facing projection and a first planar surface. The first inwardly facing projection extends inwardly between a first longitudinal end and a first lateral side of the first pocket. The first planar surface extends substantially parallel to the deck. The first planar surface is defined by the first inwardly facing projection. The first planar surface defines a maximum height of the engagement protrusion relative to the deck. The first planar surface has a non-uniform area defined at least in part by the first inwardly facing projection.

20 Claims, 17 Drawing Sheets

(58) Field of Classification Search
USPC ........................................................ 227/175.1
See application file for complete search history.

(56) References Cited

U.S. PATENT DOCUMENTS

| | | | | |
|---|---|---|---|---|
| 9,717,497 | B2 | 8/2017 | Zerkle et al. | |
| 9,808,248 | B2 | 11/2017 | Hoffman | |
| 9,839,421 | B2 | 12/2017 | Zerkle et al. | |
| 10,092,292 | B2 | 10/2018 | Boudreaux et al. | |
| 10,130,359 | B2 | 11/2018 | Hess et al. | |
| 10,166,023 | B2 | 1/2019 | Vendely et al. | |
| 10,349,939 | B2 | 7/2019 | Shelton, IV et al. | |
| 11,166,724 | B2 | 11/2021 | McGiveron et al. | |
| 11,229,433 | B2 | 1/2022 | Schings et al. | |
| 2012/0074198 | A1 * | 3/2012 | Huitema ............ | A61B 17/0682 227/176.1 |
| 2022/0387027 | A1 | 12/2022 | Shelton, IV et al. | |

FOREIGN PATENT DOCUMENTS

| | | | |
|---|---|---|---|
| EP | 3689262 | A1 | 8/2020 |
| EP | 3838171 | A2 | 6/2021 |
| WO | 2022/200990 | A1 | 9/2022 |

OTHER PUBLICATIONS

U.S. Appl. No. 18/588,147, entitled "Surgical Stapler Cartridge Having Intermediate Raised Tissue Engagement Protrusions,", filed Feb. 27, 2024.

U.S. Appl. No. 18/588,206, entitled "Surgical Stapler Cartridge Having Raised Surface to Promote Buttress Adhesion,", Filed Feb. 27, 2024.

U.S. Appl. No. 18/588,240, entitled "Surgical Stapler Cartridge Having Cartridge Retention Features,", filed Feb. 27, 2024.

U.S. Appl. No. 18/588,269, entitled "Surgical Stapler Anvil Having Staple Forming Pockets with Laterally Varying Orientations,", filed Feb. 27, 2024.

U.S. Appl. No. 18/588,684, entitled "Method of Surgical Stapling,", filed Feb. 27, 2024.

U.S. Appl. No. 18/758,887, entitled "Sled Retention and Alignment Features for Surgical Stapler,", filed Jun. 28, 2024.

U.S. Appl. No. 63/459,739, entitled "Surgical Stapler Anvil Having Staple Forming Pockets with Laterally Varying Orientations,", filed Apr. 17, 2023.

International Search Report and Written Opinion dated Aug. 22, 2024, for International Application No. PCT/IB2024/054894, 18 pages.

* cited by examiner

T1
T2
86
36
86
44
40
T
42
70

SURGICAL STAPLER CARTRIDGE HAVING TISSUE ENGAGEMENT PROTRUSIONS WITH ENLARGED ENGAGEMENT SURFACE

PRIORITY

This application claims priority of U.S. Pat. App. No. 63/467,623, entitled "Surgical Stapler Cartridge Having Tissue Engagement Protrusions with Enlarged Engagement Surface," filed May 19, 2023, the disclosure of which is incorporated by reference herein in its entirety.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion or other type of body portion, which is manipulated by the clinician or robotic operator. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

The stapling assembly (e.g., a staple cartridge) of a surgical stapler may include raised features that extend upwardly from a deck thereof for enhancing the gripping of tissue by the stapling assembly when the end effector is closed, and/or for guiding the legs of the staples as the legs exit the respective staple openings during deployment of the staples. For example, such raised features may extend upwardly from the deck at or near proximal and distal ends of each cartridge pocket. In some instances, it may also be desirable to adhere an adjunct material, such as a buttress, to the stapling assembly for deployment with the staples to reinforce the mechanical fastening of tissue provided by the deployed staples. Typically, such adjunct material is adhered directly to the deck via an adhesive material.

While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

Figure 1:
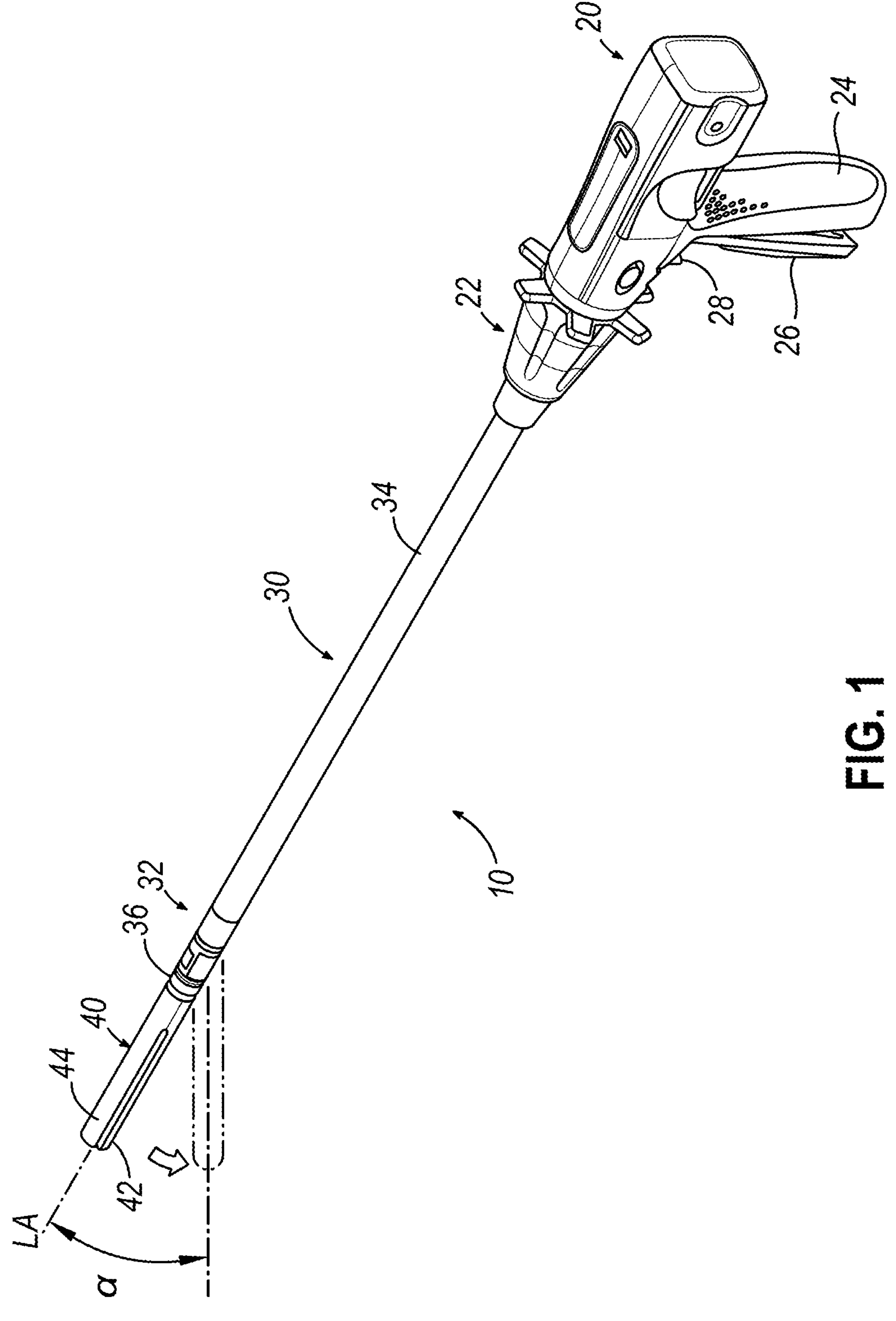
FIG. 1 depicts a perspective view of an example of a surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms “proximal” and “distal” are defined herein relative to a human or robotic operator of the surgical instrument. The term “proximal” refers the position of an element closer to the human or robotic operator of the surgical instrument and further away from the surgical end effector of the surgical instrument. The term “distal” refers to the position of an element closer to the surgical end effector of the surgical instrument and further away from the human or robotic operator of the surgical instrument. In addition, the terms “upper,” “lower,” “lateral,” “transverse,” “top,” are relative terms to provide additional clarity to the figure descriptions provided below. The terms “upper,” “lower,” “lateral,” “transverse,” “top,” are thus not intended to unnecessarily limit the invention described herein.

Furthermore, the terms “about,” “approximately,” “substantially,” and the like as used herein in connection with any numerical values, ranges of values, and/or geometric/positional quantifications are intended to encompass the exact value(s) referenced as well as a suitable tolerance that enables the referenced feature or combination of features to function for the intended purpose described herein. For example, “substantially parallel” encompasses nominally parallel structures.

As used herein in connection with any examples of end effector jaw tips, a tip described as “angled,” “bent,” or “curved” encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as “straight” encompasses tip configurations in which a longitudinal axis of the tip is substantially parallel or coaxial with the longitudinal axis of the jaw body.

I. Overview of Surgical Stapler Features

FIGS. 1-6 depict an illustrative surgical stapler (10) that is sized for insertion through a trocar cannula or a surgical incision (e.g., thoracotomy, etc.) to a surgical site in a patient for performing a surgical procedure. Surgical stapler (10) includes a body exemplified as a handle assembly (20), a shaft (30) that extends distally from handle assembly (20) along a longitudinal axis (LA) and distally terminates at an articulation joint (32), and an end effector (40) operatively coupled with shaft (30) via articulation joint (32).

Once end effector (40) and articulation joint (32) are inserted distally through the cannula passageway of a trocar, articulation joint (32) may be remotely articulated, as depicted in phantom in FIG. 1, by an articulation control exemplified as a rotatable knob (22) of handle assembly (20), such that end effector (40) may be deflected from the longitudinal axis (LA) at a desired angle (α). Articulation joint (32) and related features for manipulating articulation joint (32) may be further configured in accordance with the teachings of U.S. Pat. No. 9,186,142, entitled “Surgical Instrument End Effector Articulation Drive with Pinion and Opposing Racks,” issued on Nov. 17, 2015, the disclosure of which is incorporated by reference herein in its entirety.

End effector (40) includes a lower jaw exemplified as a cartridge jaw (42) configured to removably receive a staple cartridge (70) (also referred to as a “reload”), and an upper jaw exemplified as an anvil jaw (44) (also referred to as an “anvil”) that pivots relative to cartridge jaw (42) to clamp tissue therebetween. In other versions, end effector (40) may be alternatively configured such that cartridge jaw (42) pivots relative to anvil jaw (44). Unless otherwise described, the term “pivot” (and variations thereof) as used herein in connection with the relative motion between jaws (42, C44) encompasses but is not necessarily limited to pivotal movement about a fixed axis. For instance, in some versions, anvil jaw (44) may pivot about an axis that is defined by a pin (or similar feature) that slidably translates along an elongate slot or channel as anvil jaw (44) moves toward cartridge jaw (42). Such translation may occur before, during, or after the pivotal motion. It should therefore be understood that such combinations of pivotal and translational movement are encompassed by the term “pivot” and variations thereof as used herein with reference to the relative motion between jaws (42, C44).

As shown in FIG. 1, handle assembly (20) includes a pistol grip (24) and a closure trigger (26). Closure trigger (26) is pivotable toward pistol grip (24) to cause clamping, or closing, of anvil jaw (44) toward cartridge jaw (42) of end effector (40). Such closing of anvil jaw (44) is provided through a closure tube (34) and a closure ring (36) of shaft (30), which both longitudinally translate relative to handle assembly (20) in response to pivoting of closure trigger (26) relative to pistol grip (24). Closure tube (34) extends along the length of shaft (30); and closure ring (36) is positioned distal to articulation joint (32). Articulation joint (32) is operable to transmit longitudinal movement from closure tube (34) to closure ring (36) to actuate anvil jaw (44) relative to cartridge jaw (42).

Handle assembly (20) also includes a firing trigger (28). An elongate actuator (not shown) extends longitudinally through shaft (30) and transmits a longitudinal firing motion from handle assembly (20) to a firing member exemplified as a firing beam (46) in response to actuation of firing trigger (28). As a result, firing beam (46) translates distally through a firing stroke to cause stapling and severing of tissue clamped by end effector (40), as will be described in greater detail below. Though not shown, handle assembly (20) may further include a motor operable to actuate such firing assembly components of surgical stapler (10) in response to actuation of firing trigger (28) by a user, for example as disclosed in U.S. Pat. No. 8,453,914, entitled "Motor-Driven Surgical Cutting Instrument with Electric Actuator Directional Control Assembly," issued Jun. 4, 2013, the disclosure of which is incorporated by reference herein in its entirety.

As shown in FIGS. 2-5, firing beam (46) includes a proximal beam portion (48) and a distal knife portion (50), where distal knife portion (50) may be integrally formed with a distal end of proximal beam portion (48), or separately formed and thereafter securely affixed to the distal end of proximal beam portion (17). Distal knife portion (50) includes a transversely oriented upper protrusion exemplified as an upper pin (52), a transversely oriented lower protrusion exemplified as a cap (54), a transversely oriented middle protrusion exemplified as a middle pin (56), and a distally presented cutting edge (58). Upper pin (52) is slidable within a longitudinal anvil jaw slot (62) of anvil jaw (44) and cap (54) is slidable along a lower surface of cartridge jaw (42) defined by a longitudinal cartridge jaw slot (64). Middle pin (56) is slidable along a top surface of cartridge jaw (42) and cooperates with cap (54) to stabilize and guide distal knife portion (50) along a longitudinal firing stroke. Firing beam (46) may be further configured and operable in accordance with the teachings of U.S. Pat. No. 9,717,497, entitled "Lockout Feature for Movable Cutting Member of Surgical Instrument," issued Aug. 1, 2017, the disclosure of which is incorporated by reference herein in its entirety.

Figure 2:
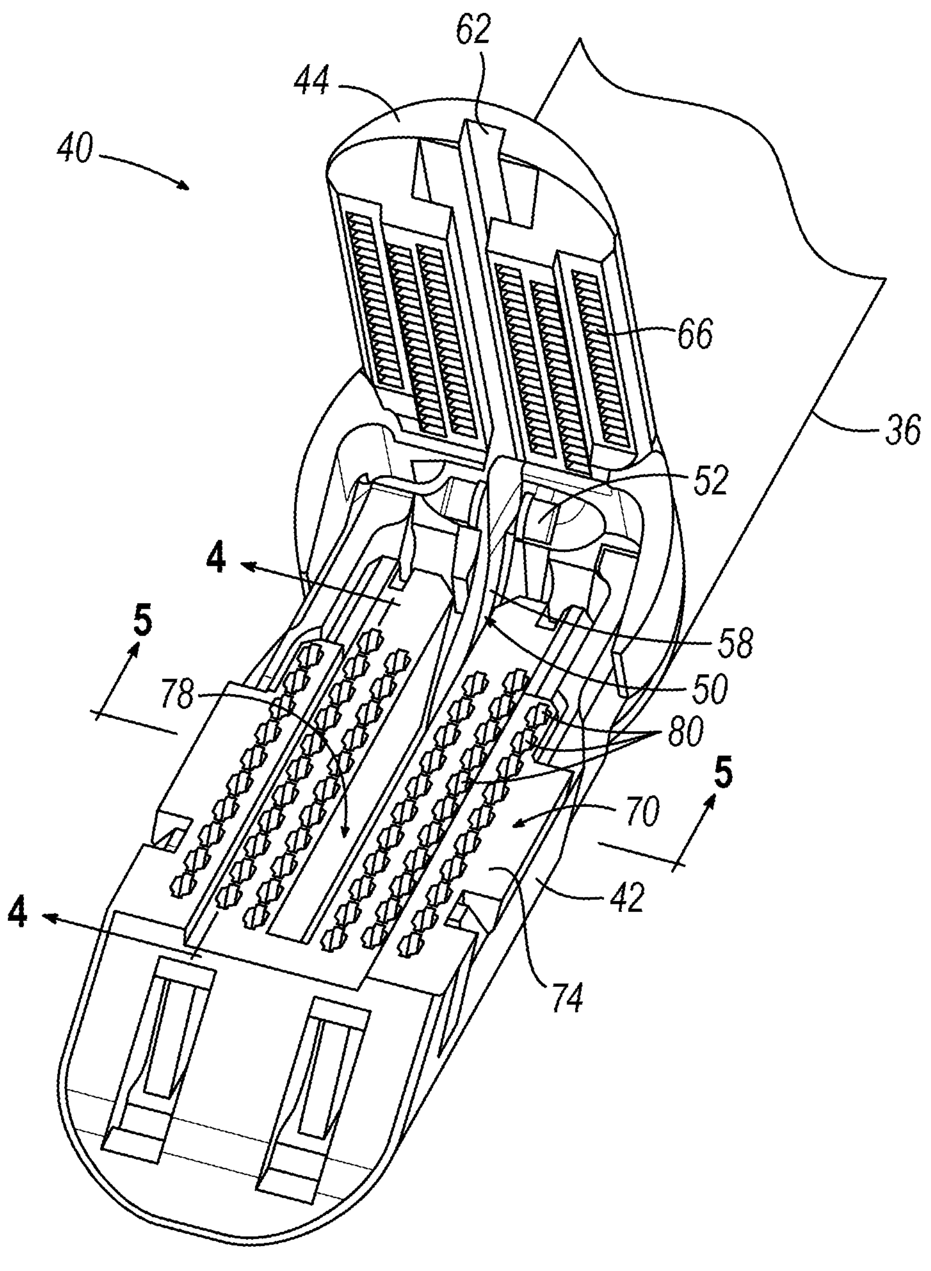
FIG. 2 depicts a perspective view of an end effector of the surgical stapler of FIG. 1, shown in an open state.
Figure 3:
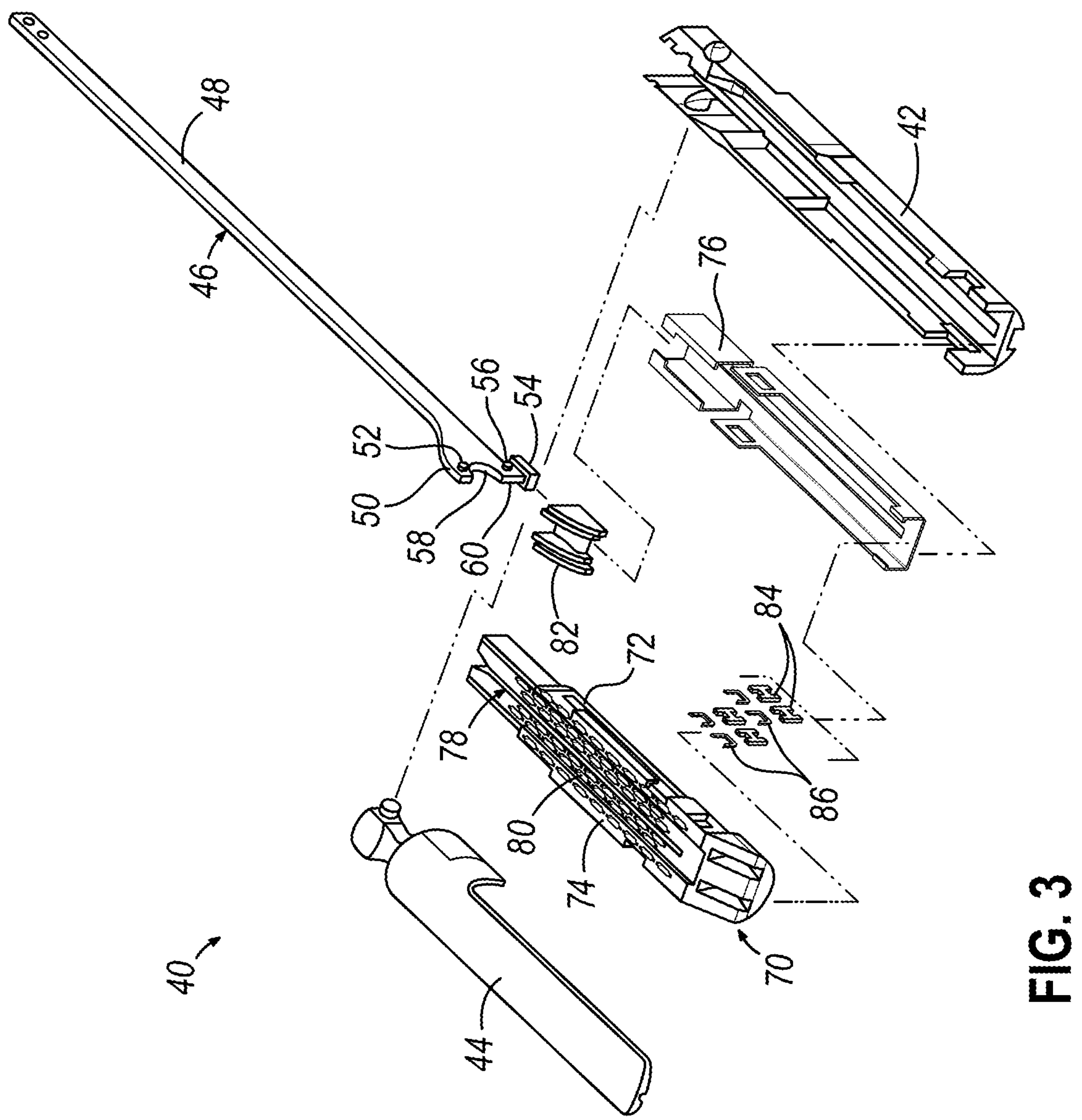
FIG. 3 depicts an exploded perspective view of the end effector of FIG. 2.

FIG. 2 shows anvil jaw (44) pivoted to an open state with firing beam (46) proximally positioned, which permits an unspent (i.e., unfired) staple cartridge (70) to be removably installed into a channel of cartridge jaw (42). As best seen in FIGS. 2-3, staple cartridge (70) includes a cartridge body (72) that presents an upper deck (74) defining a first stapling surface, and a lower pan (76) (also referred to as a "tray") coupled to an underside of cartridge body (72). A vertical knife slot (78) extends longitudinally through cartridge body (72) and is configured to slidably receive distal knife portion (50) of firing beam (46). In the present version, three rows of cartridge pockets (80) (also referred to as "staple openings," "staple apertures," or "staple cavities") are formed through upper deck (74) along each lateral side of knife slot (78).

Figure 4A:
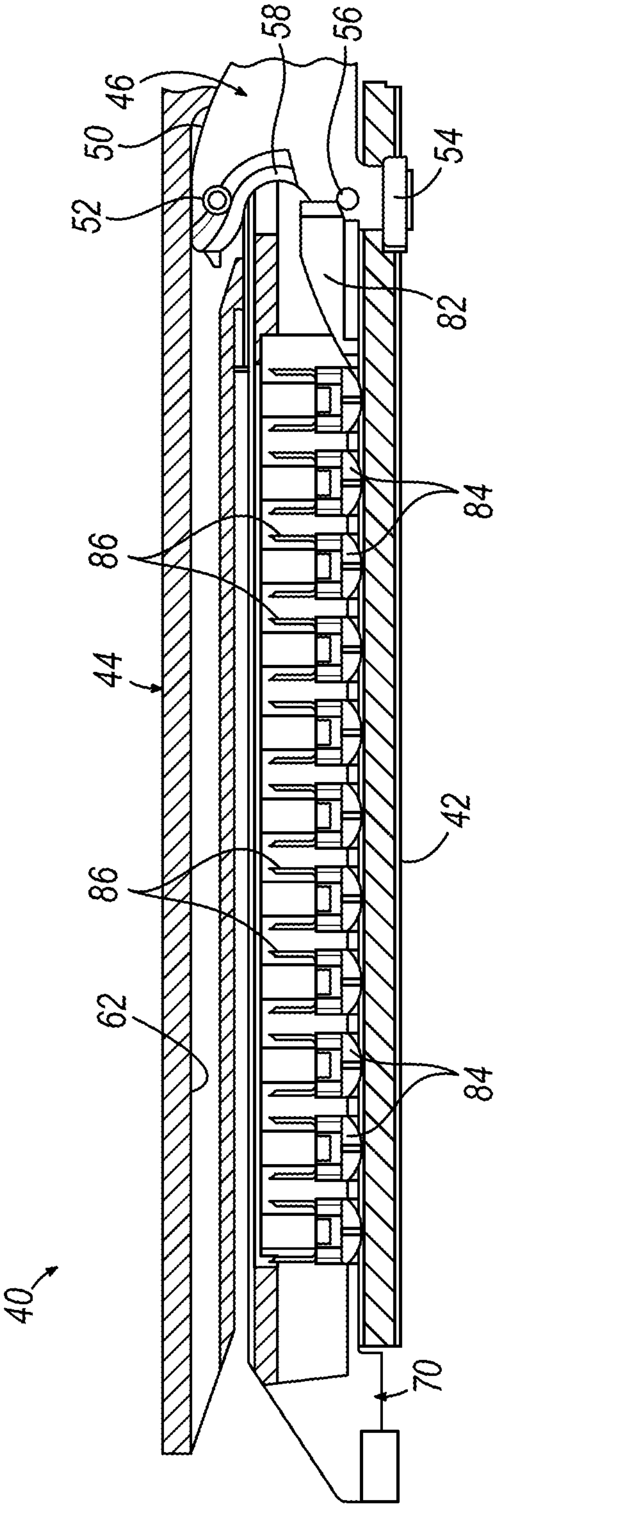
FIG. 4A depicts a side cross-sectional view of the end effector of FIG. 2, taken along line 4-4 of FIG. 2, showing a firing beam and sled in a proximal unfired position.
Figure 4B:
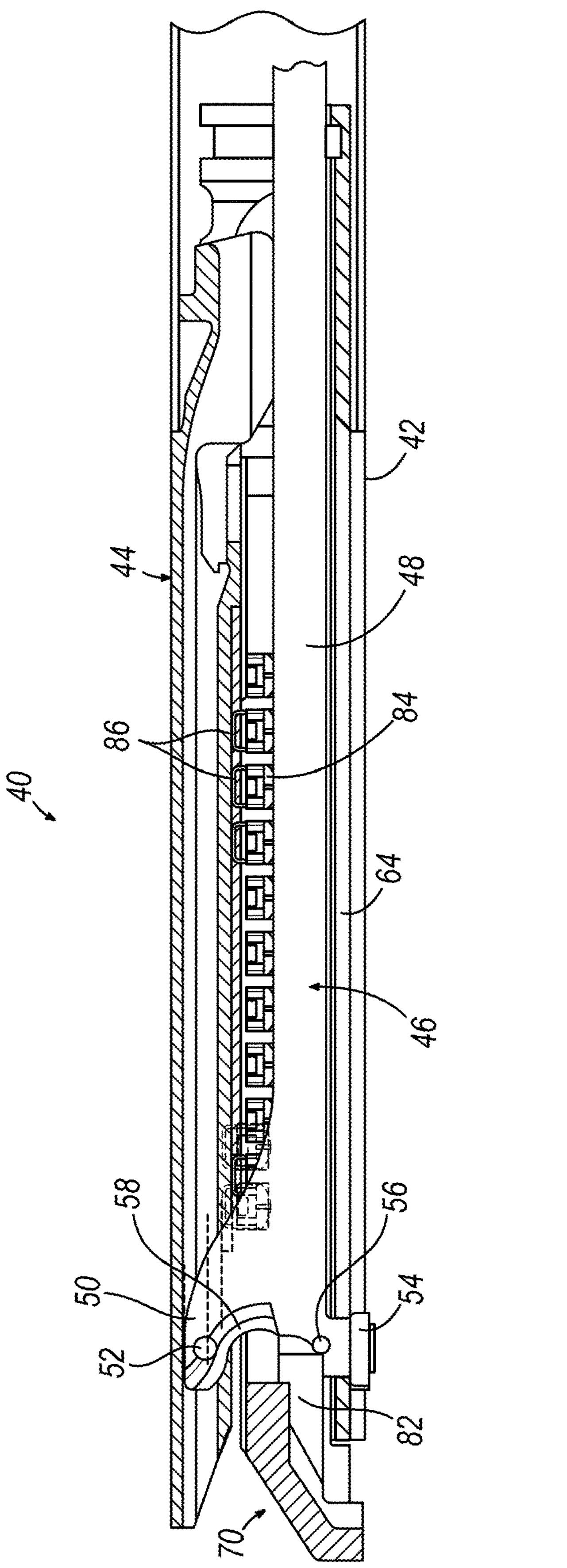
FIG. 4B depicts a side cross-sectional view of the end effector of FIG. 2, taken along line 4-4 of FIG. 2, showing the firing beam and sled in a distal fired position.
Figure 5:
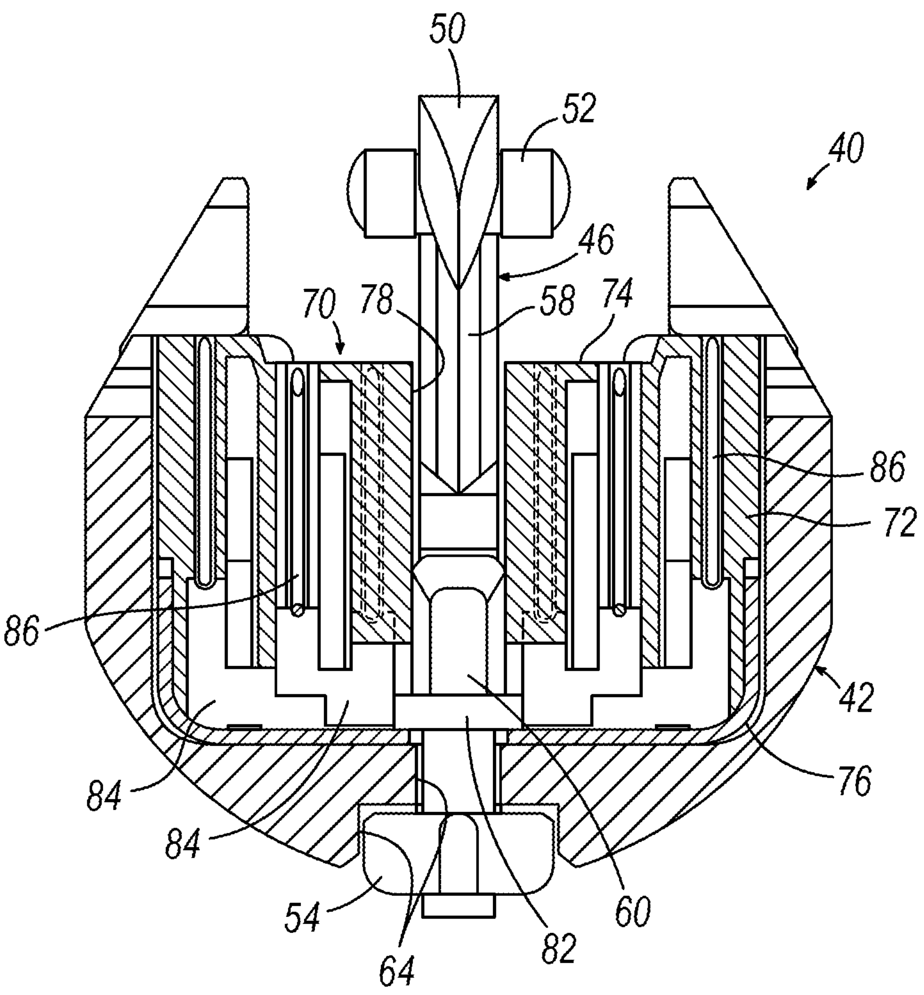
FIG. 5 depicts an end cross-sectional view of the end effector of FIG. 2, taken along line 5-5 of FIG. 2 and omitting an upper anvil jaw, showing further details of a distal knife portion of the firing beam and the sled.

As shown in FIGS. 3-5, staple cartridge (70) further includes a sled (82) (also referred to as a "wedge sled") and a plurality of staple drivers (84) that are movably captured between cartridge body (72) and pan (76). Each staple driver (84) is aligned with and movable vertically within a respective cartridge pocket (80). Staples (86) are positioned within respective cartridge pockets (80) above respective staple drivers (84). During a firing stroke, sled (82) is actuated longitudinally within staple cartridge (70) by distal knife portion (50) from a proximal position shown in FIG. 4A to a distal position shown in FIG. 4B. Angled cam surfaces of sled (82) cam staple drivers (84) vertically upwardly within cartridge pockets (80) to drive staples (86) upwardly above deck (74), thereby ejecting staples (86) from cartridge pockets (80) and toward anvil jaw (44).

More specifically, with end effector (40) closed as shown in FIGS. 4A-4B, firing beam (46) is actuated distally into engagement with anvil jaw (44) by directing upper pin (52) into longitudinal anvil slot (62). A distal end projection (60) (see FIG. 5) of distal knife portion (50) of firing beam (46) engages a proximal end of sled (82) and drives sled (82) distally as distal knife portion (50) is advanced distally through staple cartridge (70) in response to actuation of firing trigger (28). During such firing, distal knife portion (50) advances distally along knife slot (78) of staple cartridge (70) so that cutting edge (58) severs tissue clamped between staple cartridge (70) and anvil jaw (44).

As shown in FIGS. 4A-4B, middle pin (56) and distal end projection (60) together actuate staple cartridge (70) by entering into knife slot (78), driving sled (82) into camming contact with staple drivers (84) to thereby actuate staple drivers (84) upwardly, which in turn drives staples (86) outwardly through cartridge pockets (80), through clamped tissue, and into forming contact with staple forming pockets (66) (see FIG. 2) on a second stapling surface defined by anvil jaw (44). Such stapling of tissue prompted by the camming interaction between sled (82) and staple drivers (84) is performed concurrently with the severing of tissue performed by cutting edge (58). However, it will be appreciated that for each longitudinal section of tissue clamped by end effector (40), staples (86) may be ejected into the tissue slightly before cutting edge (58) severs the tissue to ensure that the tissue is stapled and thus sealed before being severed. FIG. 4B depicts firing beam (46) fully distally translated at the end of a firing stroke after the tissue clamped by end effector (40) has been stapled and severed.

Staple cartridge (70) and anvil jaw (44) may be further configured and operable in accordance with the teachings of U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; U.S. Pat. No. 10,092,292, entitled "Staple Forming Features for Surgical Stapling Instrument," issued Oct. 9, 2018; and/or U.S. Pat. No. 10,130,359, entitled "Method for Forming a Staple," issued Nov. 20, 2018, the disclosure of each of which is incorporated by reference herein in its entirety.

Figure 6:
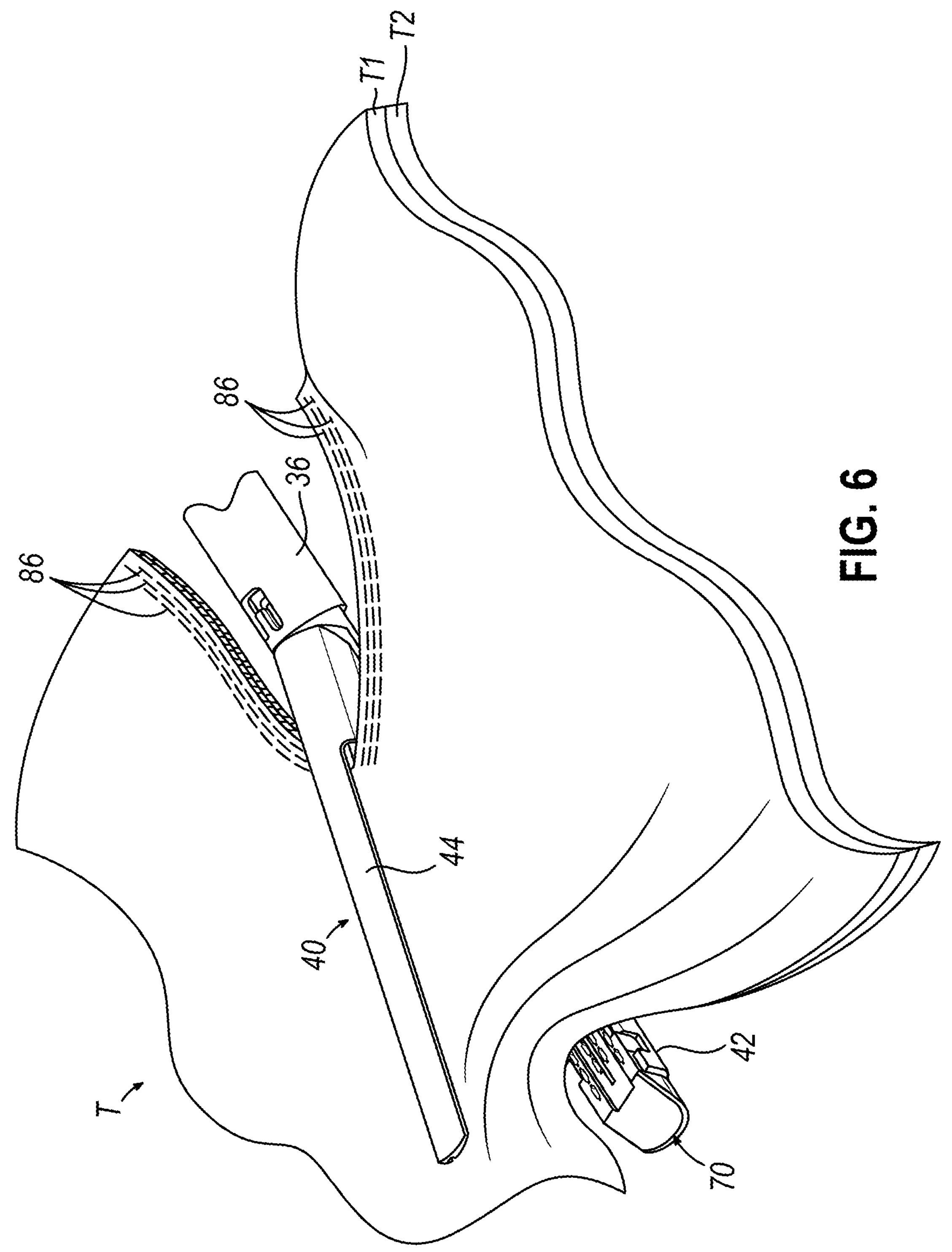
FIG. 6 depicts a perspective view of the end effector of FIG. 2, shown after having been fired once on a first section of tissue and being positioned to clamp and fire on a second section on tissue.

FIG. 6 shows end effector (40) having been actuated through a single firing stroke on tissue (T) having first and second layers (T1, T2). Cutting edge (58) (see FIGS. 2-5) has cut through tissue (T) while staple drivers (84) have driven three alternating rows of staples (86) through tissue (T) on each side of the cut line produced by cutting edge (58). After the first firing stroke is complete, end effector (40) is withdrawn from the patient, spent staple cartridge (70) is replaced with a new unspent staple cartridge (70), and end effector (40) is then again inserted into the patient to reach the stapling site for further cutting and stapling. This process may be repeated until the desired quantity and pattern of firing strokes across the tissue (T) has been completed.

II. Examples of Stapling Assemblies Including Engagement Protrusions

In some instances, it may be desirable in predetermined areas to incorporate raised features that extend upwardly from the deck thereof for enhancing the gripping of tissue by the stapling assembly (e.g., a staple cartridge) when the end effector is closed, and/or for guiding the legs of the staples as the legs exit the respective staple openings during deployment of the staples. Utilizing raised features in predetermined areas may provide increased localized compression applied to tissue (T) in those predetermined areas while simultaneously minimizing the overall increase in total compression applied to tissue (T). It may be desirable to affect the interaction between the raised feature(s) and tissue (T) or between the raised features and a buttress. For example, it may be desirable to resist relative movement between the buttress to the deck prior to contacting tissue, and encourage release of the buttress and/or tissue from the raised features after contacting tissue.

It will be understood that while the features shown and described above are presented in the context of a stapling assembly (e.g., a staple cartridge (C110)) for surgical stapler (10), such features may also be applied to staple cartridges configured for use with various other types of surgical staplers, such as linear surgical staplers. Staple cartridge (C110) described below provides such functionality. FIGS. 7-18 are shown to scale.

A. Example of Staple Cartridge

Figure 7:
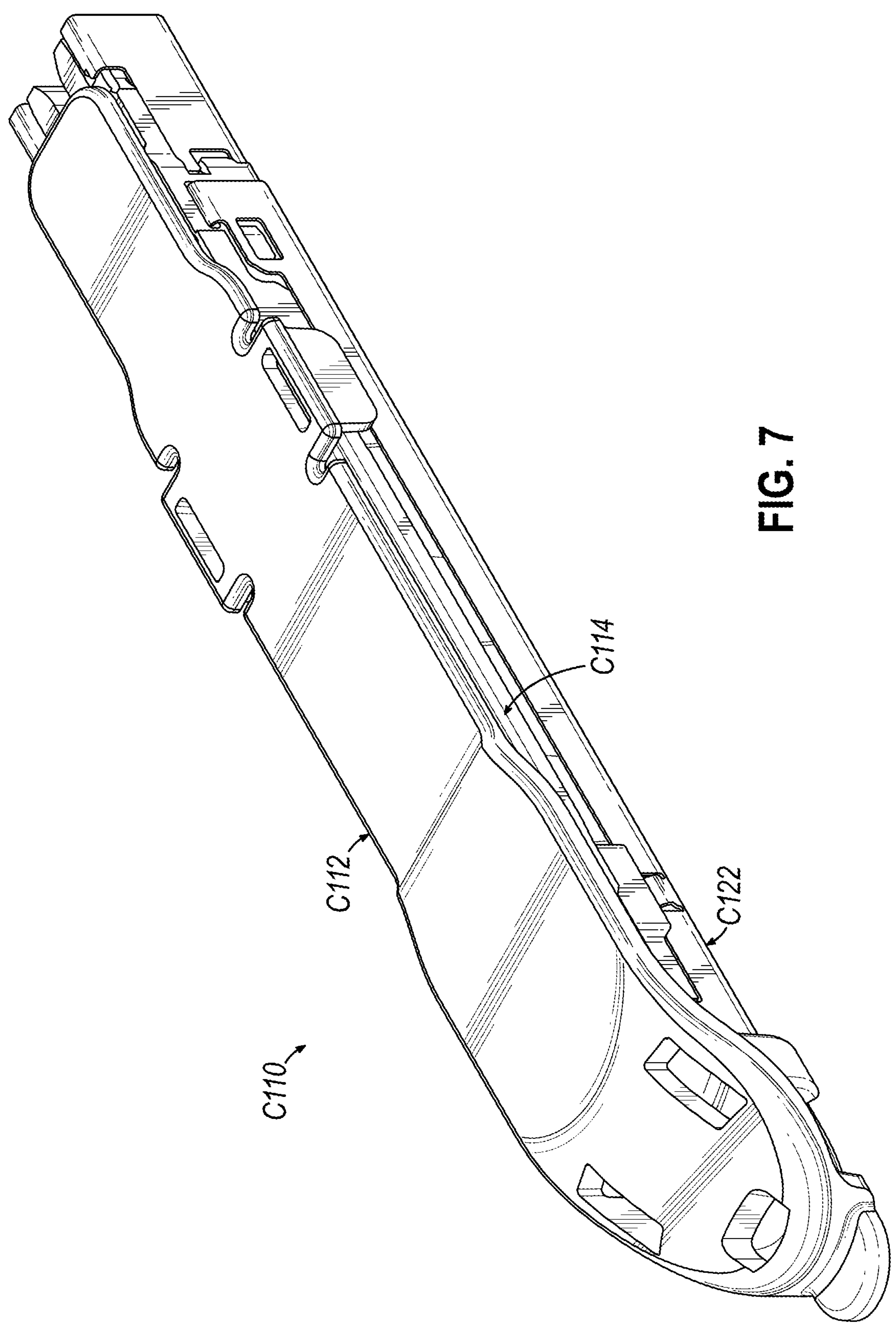
FIG. 7 depicts a perspective view of another example of a staple cartridge for use with the end effector of FIG. 2.
Figure 8:
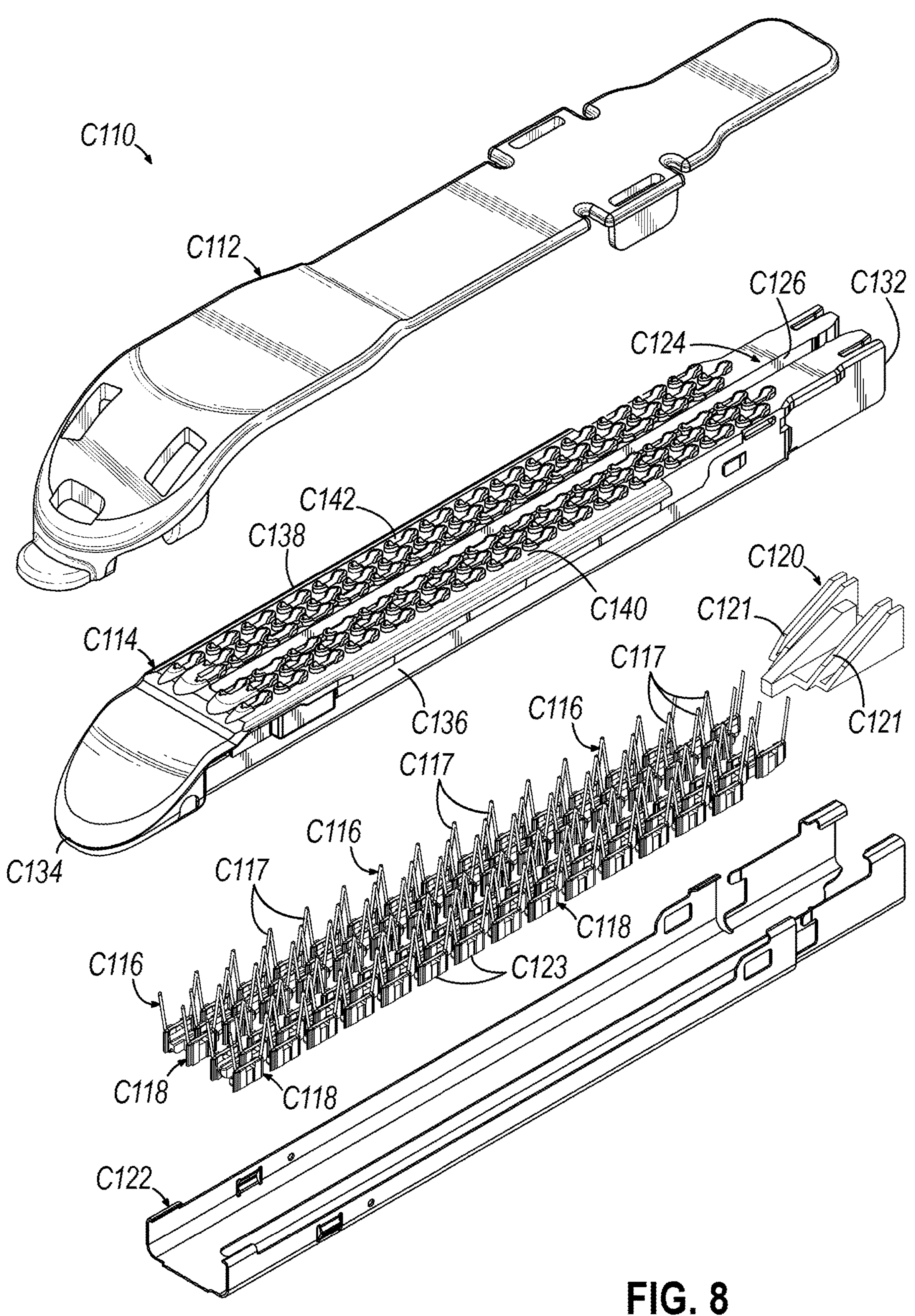
FIG. 8 depicts an exploded perspective view of the staple cartridge of FIG. 7, where the staple cartridge includes a retainer, a cartridge body, staples, staple drivers, a sled, and a tray.

FIGS. 7-18 show an example of a staple cartridge (C110) configured for use with end effector (40) of FIG. 2. As shown in FIGS. 7-8, staple cartridge (C110) includes a retainer (C112), a cartridge body (C114), a plurality of staples (C116), a plurality of staple drivers (C118), a wedge sled (C120), and a tray (C122). Staple cartridge (C110) is similar to staple cartridge (C70) described above except as otherwise described below. Staple cartridge (C110) is configured to deploy staples (C116) toward corresponding staple forming pockets of an anvil (not shown), but similar to staple forming pockets (C66) of anvil (44). Staples (C116) are similar to staples (C86), and staple drivers are similar to staple drivers (C118). Tray (C122) is similar to lower tray (C76). Tray (C122) encloses an underside of cartridge body (C114) to retain staples (C116) and staple drivers (C118) within staple cartridge (C110). Wedge sled (C120) is similar to wedge sled (C82) and is slidably disposed within cartridge body (C114). Wedge sled (C120) includes upwardly presented cam surfaces (C121) configured to engage the undersides (C123) of staple drivers (C118).

As will be described in greater detail below, cartridge body (C114) includes a deck (C124), an elongate slot (C126) formed in deck (C124), a plurality of cartridge pockets (C128) formed in deck (C124), and a plurality of engagement protrusions (C130*a-f*) extending outwardly from deck (C124). Cartridge body (C114) includes a proximal end (C132), a distal end (C134), a first lateral side (C136), and a second lateral side (C138). Second lateral side (C138) of cartridge body (C114) is disposed opposite first lateral side (C136). Deck (C124) is similar to upper deck (C74) and is configured to compress tissue (T) against an anvil (not shown), but similar to anvil (44). Deck (C124) is defined by cartridge body (C114) and is shown as being substantially planar. Elongate slot (C126) is similar to knife slot (C78). Elongate slot (C126) extends along a longitudinal axis (LA) of cartridge body (C114). Elongate slot (C126) opens upwardly through deck (C124) and terminates at a connecting portion (C131). Elongate slot (C126) is configured to slidably receive a knife therein. The knife may be a distal knife portion of a firing beam (not shown), such as distal knife portion (C50) of firing beam (C46). Cartridge pockets (C128) are configured to house a plurality of staples (C116). As shown, each cartridge pocket (C128) slidably houses an unformed staple (C116) and a respective staple driver (C118) similar to staple drivers (C84) positioned beneath staples (C86). While FIG. 8 shows a 1:1 relationship of cartridge pockets (C128) to staples (C116), this may vary.

Figure 9:
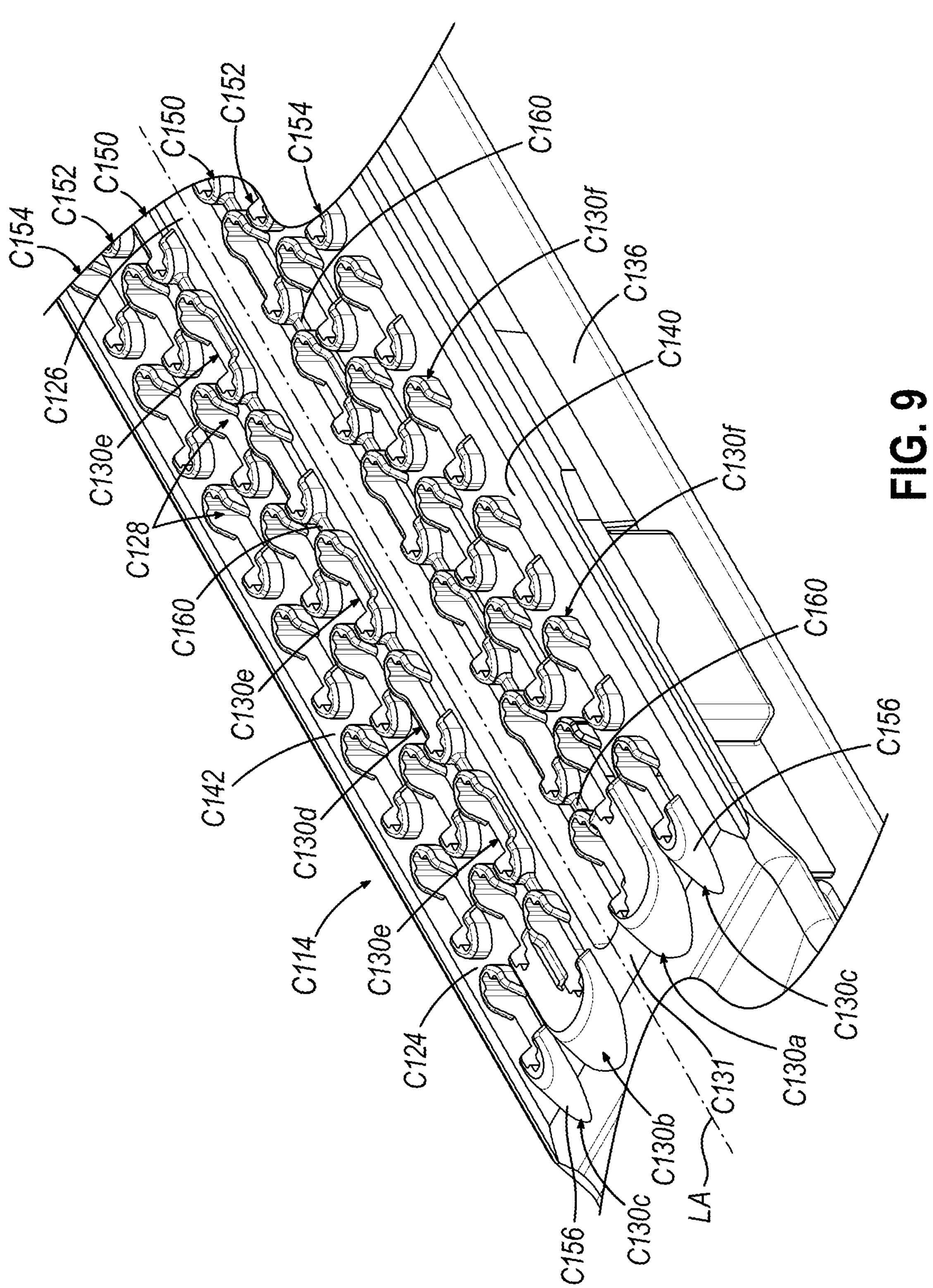
FIG. 9 depicts a perspective view of an enlarged portion of the cartridge body of FIG. 8.
Figures 10, 11:
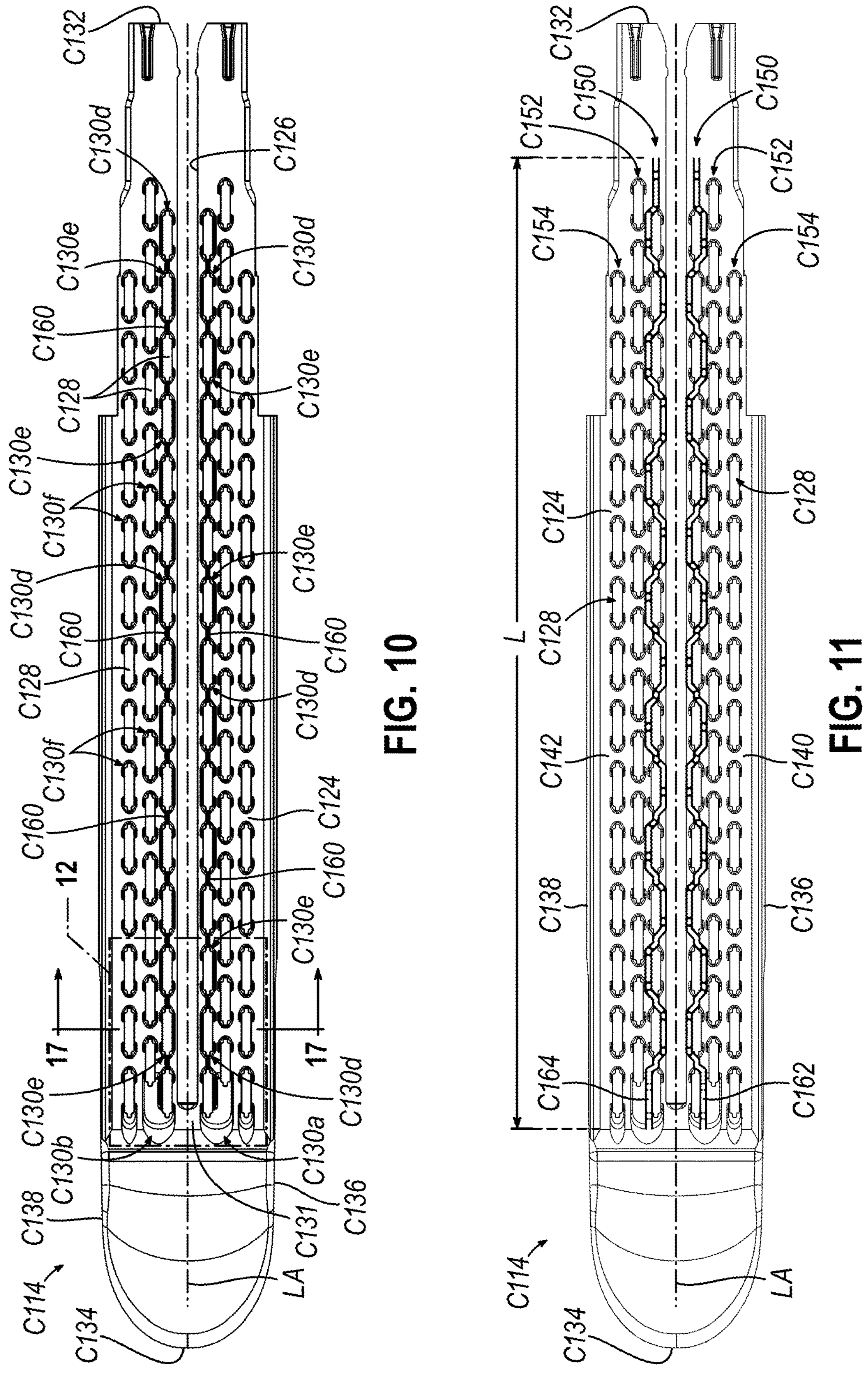
FIG. 10 depicts a top plan view of the cartridge body of FIG. 8.
FIG. 11 depicts a top plan view of the cartridge body of FIG. 10 but showing first and second continuous non-linear paths having first and second continuous non-linear cross-sectional areas along the length of inner rows of cartridge pockets.
Figure 12:
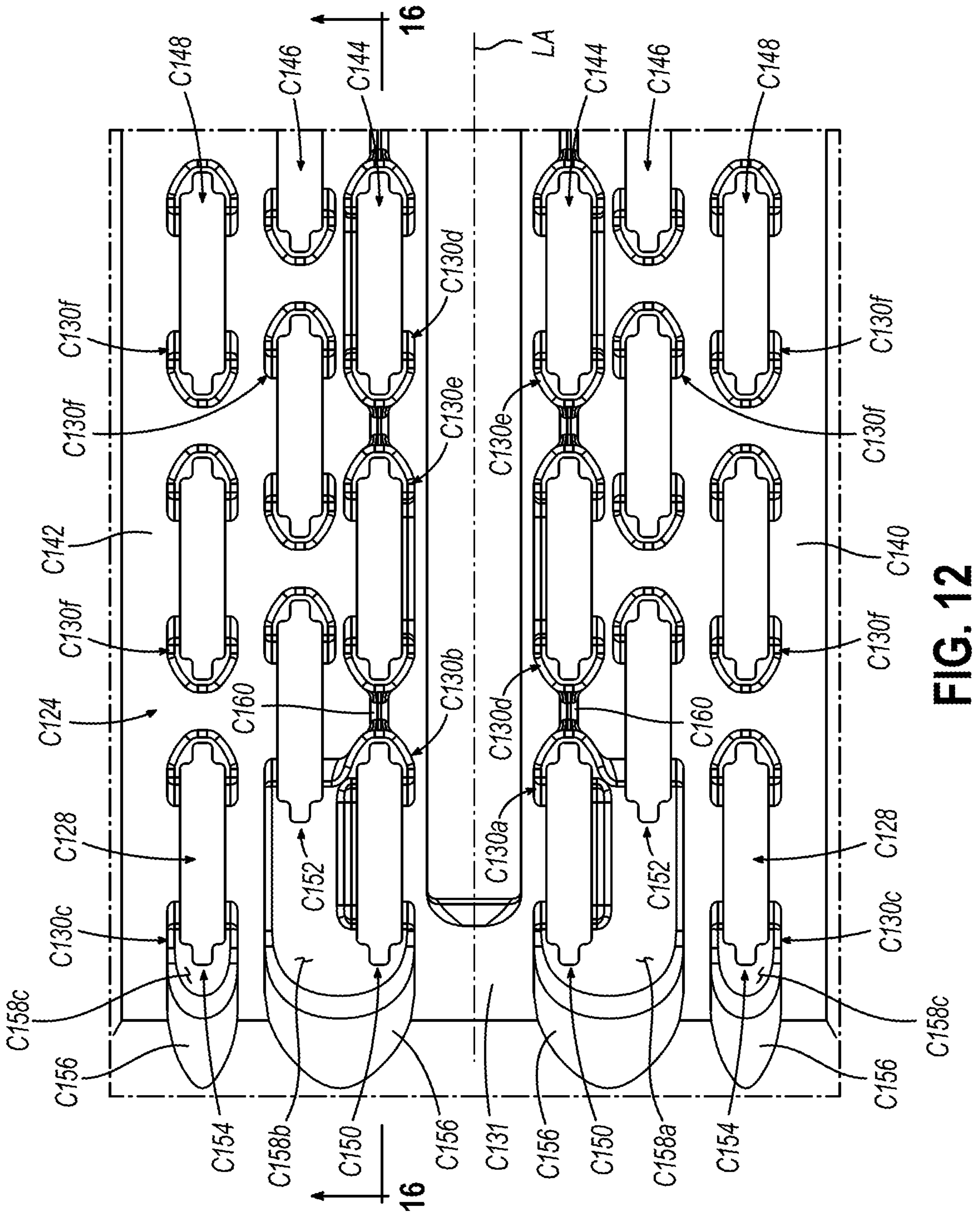
FIG. 12 depicts an enlarged partial top plan view of the cartridge body of FIG. 10.

FIG. 10 shows cartridge pockets (C128) arranged into six longitudinally extending rows. Elongate slot (C126) separates three rows positioned on a first deck side (C140) from three additional rows are positioned a second deck side (C142). Second deck side (C142) of deck (C124) is a mirror image of first deck side (C140). As shown in FIGS. 9 and 12, these longitudinal rows include inner rows (C144), middle rows (C146), and outer rows (C148). While two inner rows (C144), two middle rows (C146), and two outer rows (C148) are shown, more or fewer rows are envisioned. Inner rows (C144) are the closest cartridge pockets (C128) relative to elongate slot (C126). In other words, inner rows (C144) are positioned closer to elongate slot (C126) than middle rows (C146). Similarly, middle rows (C146) are positioned closer to elongate slot (C126) than outer rows (C148) of cartridge pockets (C128). Elongate slot (C126) separates and bisects inner rows (C144) of cartridge pockets (C128). Inner rows (C144) and middle rows (C146) are shown as including fifteen cartridge pockets (C128); however, more or fewer cartridge pockets (C128) are envisioned. Outer rows (C148) are shown as including fourteen cartridge pockets (C128); however, more or fewer cartridge pockets (C128) are envisioned.

As shown in FIGS. 9 and 12, engagement protrusions (C130*a-f*) extend from deck (C124) and are configured to grip tissue (T) or an adjunct material (e.g., a buttress) positioned thereon. As will be described below, cartridge body (C114) includes six different configurations of engagement protrusions (C130*a-f*). The arrangement of these engagement protrusions (C130*a-f*) is symmetric about elongate slot (C126). Each engagement protrusion (C130*a-f*) partially surrounds a respective cartridge pocket (C128). Similar to cartridge pockets (C128), engagement protrusions (C130*a-f*) are arranged into a plurality of longitudinally extending rows. These longitudinal rows include inner rows (C150), middle rows (C152), and outer rows (C154). While two inner rows (C150), two middle rows (C152), and two outer rows (C154) are shown, more or fewer rows are also envisioned. Inner rows (C150) generally correspond with inner rows (C144) of cartridge pockets (C128). Similarly, middle rows (C152) generally correspond with middle rows (C146) of cartridge pockets (C128), and outer rows (C154) generally correspond with outer rows (C148) of cartridge pockets (C128). Inner rows (C150) are the closest engagement protrusions relative to elongate slot (C126). In other words, inner rows (C150) of engagement protrusions are positioned closer to elongate slot (C126) than middle rows (C152), and middle rows (C152) are positioned closer to elongate slot (C126) than outer rows (C154) of engagement protrusions. As shown, inner rows (C150), middle rows (C152), and outer rows (C154) each extend substantially parallel to elongate slot (C126).

As best shown in FIGS. 9 and 12, engagement protrusions (C130*a-c*) are the distal most engagement protrusions. Each engagement protrusion (C130*a-c*) includes a distal lead-in portion (C156). Engagement protrusions (C130*a-b*) extend between multiple rows. Particularly, engagement protrusion (C130*a*) extends between inner row (C150) and middle row (C152) on first deck side (C140). Similarly, engagement protrusion (C130*b*) extends between inner row (C150) and middle row (C152) on second deck side (C142). Engagement protrusions (C130*a-c*) include planar surfaces (C158*a-c*) (see FIG. 12). Engagement protrusions (C130*c*) are the distal most engagement protrusions for outer rows (C154) on first and second deck sides (C140, C142). Each engagement protrusion (C130*c-f*) extends within a single row (e.g., one of inner row (C150), middle row (C152), and outer rows (C154)) and does not connect with an adjacent row. As shown, longitudinally adjacent engagement protrusions (C130*d-f*) of inner rows (C150) on first and second deck sides (C140, C142) are linked together (also referred to as joined together) by interconnections (C160). Interconnections (C160) effectively daisy chain together adjacent engagement protrusions (C130*d-f*) of inner rows (C150).

As shown in FIG. 10, inner row (C150) on first deck side (C140) includes engagement protrusion (C130*a*) followed by interconnection (C160), engagement protrusion (C130*d*), interconnection (C160), and engagement protrusion (C130*e*) in an alternating manner. Particularly, moving proximally, this arrangement is engagement protrusion (C130*a*), interconnection (C160), engagement protrusion (C130*d*), interconnection (C160), engagement protrusion (C130*c*), interconnection (C160), engagement protrusion (C130*d*), interconnection (C160), engagement protrusion (C130*c*), interconnection (C160), engagement protrusion (C130*d*), interconnection (C160), engagement protrusion (C130*e*), interconnection (C160), engagement protrusion (C130*d*), interconnection (C160), engagement protrusion (C130*c*), interconnection (C160), engagement protrusion (C130*d*), interconnection (C160), engagement protrusion (C130*e*), interconnection (C160), engagement protrusion (C130*d*), interconnection (C160), engagement protrusion (C130*c*), interconnection (C160), engagement protrusion (C130*d*), interconnection (C160), and engagement protrusion (C130*c*). Moving proximally, inner row (C150) on second deck side (C142) includes engagement protrusion (C130*b*) followed by interconnection (C160), engagement protrusion (C130*e*), interconnection (C160), and engagement protrusion (C130*d*) in an alternating manner. This difference is because inner row (C150) of second deck side (C142) is a mirror image of inner row (C150) of first deck side (C140). While inner rows (C150) are shown as alternating every engagement protrusion, it is also envisioned that this pattern may vary (e.g., two engagement protrusions (C130*d*) followed by two engagement protrusions (C130*c*) each separated by interconnections (C160) etc.).

Moving proximally, middle row (C152) on first deck side (C140) includes engagement protrusion (C130*a*) followed by a series of longitudinally extending engagement protrusions (C130*f*). Moving proximally, middle row (C152) on second deck side (C142) includes engagement protrusion (C130*b*) followed by a series of longitudinally extending engagement protrusions (C130*f*). As shown, no longitudinally adjacent engagement protrusion (C130*a*-C130*f*) of middle rows (C152) is joined together by an interconnection (C160) or any other feature extending from deck (C124). Moving proximally, outer rows (C148) include engagement protrusion (C130*c*) followed by a series of longitudinally extending engagement protrusions (C130*f*). Similarly, no longitudinally adjacent engagement protrusion (C130*c*, C130*f*) of outer rows (C154) is joined together by an interconnection (C160) or any other feature extending from deck (C124). Except for engagement protrusion (C130*a*) connecting inner and middle rows (C150, C152) on first deck side (C140) and engagement protrusion (C130*b*) connecting inner and middle rows (C150, C152) on second deck side (C142), inner rows (C150) are not otherwise linked with either middle row (C146) or outer row (C148) above deck (C124). Engagement protrusions (C130*a-f*) and interconnections (C160) are integrally formed together as a unitary piece with deck (C124).

FIG. 11 shows first and second continuous non-linear raised cross-sectional areas (C162, C164) forming first and second continuous non-linear paths. First continuous non-linear raised cross-sectional area (C162) extends from deck (C124) between adjacent engagement protrusions (C130*a*, C130*d*, C130*e*) joined by interconnections (C160) along an entire length (L) of inner row (C144) of cartridge pockets (C128). Second continuous non-linear raised cross-sectional area (C164) extends from deck (C124) between adjacent engagement protrusions (C130*a*, C130*d*, C130*e*) joined by interconnections (C160) along entire length (L) of inner row (C144) of cartridge pockets (C128). First and second continuous non-linear raised cross-sectional areas (C162, C164) are configured to provide increased stiffness to inner rows (C150) of engagement protrusions (C130*a-b*, C130*d-e*). First and second continuous non-linear raised cross-sectional areas (C162, C164) increase localized clamping pressure along each adjacent side elongate slot (C126). While first and second continuous non-linear raised cross-sectional areas (C162, C164) are shown as extending along entire length (L) of inner row (C144) of cartridge pockets (C128), first and/or second continuous non-linear raised cross-sectional areas (C162, C164) may extend along a select portion of inner row (C144) of cartridge pockets (C128) that is less than entire length (L) of inner row (C144).

Figure 13:
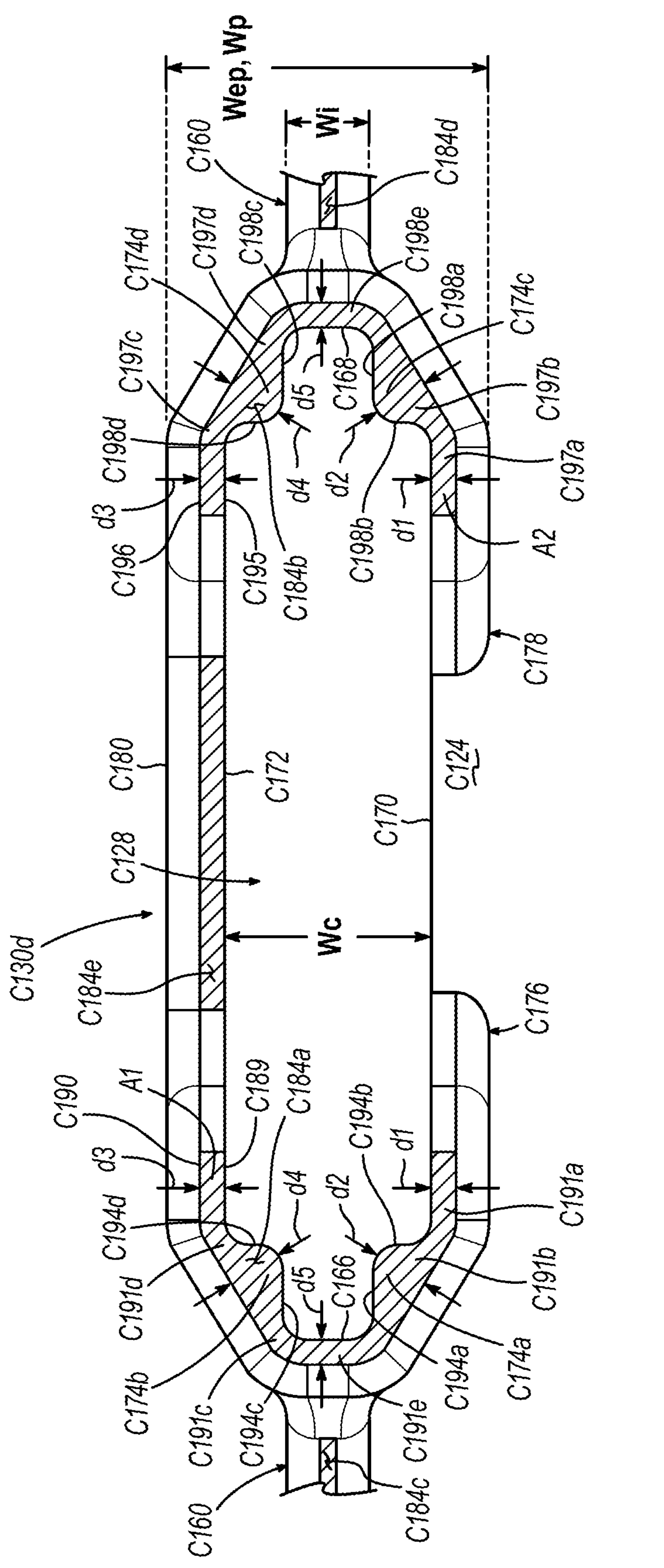
FIG. 13 depicts an enlarged top view of an engagement protrusion and accompanying interconnections partially surrounding a cartridge pocket of the cartridge body of FIG. 12.

FIG. 13 shows an enlarged top view of cartridge pocket (C128), engagement protrusion (C130*d*), and adjacent interconnections (C160) of inner rows (C150) of FIGS. 9 and 12. Engagement protrusion (C130*d*) is associated with cartridge pocket (C128). Cartridge pocket (C128) includes a first longitudinal end (C166), a second longitudinal end (C168), a first lateral side (C170), and a second lateral side (C172). Between first and second ends (C166, C168) and first and second lateral sides (C170, C172) are inwardly facing projections (C174*a-d*) of engagement protrusions (C130*a-f*). Second longitudinal end (C168) is disposed opposite first longitudinal end (C166). First and second ends (C166, C168) and inwardly facing projections (C174*a-d*) are configured to guide legs (C117) of staples (C116). First lateral side (C170) is disposed between first and second ends (C166, C168). Second lateral side (C172) is disposed between first and second ends (C166, C168) and opposite to first lateral side (C170). As shown, first and second lateral sides (C170, C172) of cartridge pocket (C128) extend substantially parallel to elongate slot (C126).

With continued reference to FIG. 13, engagement protrusion (C130*d*) includes a first end portion (C176), a second end portion (C178), and a lateral portion (C180). First end portion (C176) wraps around first longitudinal end (C166) of cartridge pocket (C128). Similarly, second end portion (C178) wraps around second longitudinal end (C168) of cartridge pocket (C128). Lateral portion (C180) extends longitudinally between first and second end portions (C176, C178) longitudinally along at least one of first or second lateral sides (C170, C172) of cartridge pocket (C128). For example, the lateral portion may extend longitudinally between first and second end portions (C176, C178) along first lateral side (C170), the lateral portion may extend longitudinally between first and second end portions (C176, C178) along second lateral side (C172), or the lateral portion may extend longitudinally between first and second end portions (C176, C178) along both of first and second lateral sides (C170, C172). As shown, lateral portion (C180) extends longitudinally along second lateral side (C172) of cartridge pocket (C128). Engagement protrusion (C130*d*) does not extend along first lateral side (C170) of cartridge pocket (C128) such that first lateral side (C170) opens directly to deck (C124). Lateral portion (C180) extends continuously between first and second end portions (C176, C178) of engagement protrusion (C130*d*). Interconnections (C160) extend continuously between second end portion (C178) of engagement protrusion (C130*d*) and a first end portion (C176) of an adjacent engagement protrusion (e.g., engagement protrusions (C130*a-b*, C130*e*)). Interconnections (C160) and lateral portion (C180) being adjacent to elongate slot (C126) provide additional compression near the cutline and assist in preventing movement of tissue (T) during firing.

As previously described, engagement protrusions (C130*a-f*) are associated with cartridge pockets (C128). First and second lateral sides (C170, C172) extend substantially parallel to elongate slot (C126). Engagement protrusions (C130*a-f*) at least partially surround respective cartridge pockets (C128). First end portion (C176) is tapered inwardly towards the first longitudinal end (C166) such that the first end portion (C176) is narrower at the first longitudinal end (C166) than at the first and second lateral sides (C170, C172) of the cartridge pocket (C128). More specifically, the portions of the first end portion (C176) that extend from the first and second lateral sides (C170, C172) towards the first longitudinal end (C166) provide a substantially frustoconical shape for the first end portion (C176) at the first longitudinal end (C166). First end portion (C176) includes a first inwardly facing projection (C174*a*), a second inwardly facing projection (C174*b*), and a first planar surface (C184*a*). First inwardly facing projection (C174*a*) extends inwardly between first longitudinal end (C166) and first lateral side (C170). First inwardly facing projection (C174*a*) extends toward second longitudinal end (C168) and second lateral side (C172) of cartridge pocket (C128). Second inwardly facing projection (C174*b*) extends inwardly between first longitudinal end (C166) and second lateral side (C172). Second inwardly facing projection (C174*b*) extends toward second longitudinal end (C168) and first lateral side (C170).

First planar surface (C184*a*) wraps around first longitudinal end (C166) of cartridge pocket (C128). First planar surface (C184*a*) defines a maximum height (hep) of engagement protrusion (C130*a-f*) relative to deck (C124). First planar surface (C184*a*) extends substantially parallel to deck (C124). First planar surface (C184*a*) is partially defined by first inwardly facing projection (C174*a*). First planar surface (C184*a*) has a non-uniform area (A1) (shown by shaded region) defined at least in part by first inwardly facing projection (C174*a*). As shown, first planar surface (C184*a*) has a non-uniform area (A1) due to first and second inwardly facing projections (C174*a-b*). First planar surface (C184*a*) includes an inner boundary (C189), an outer boundary (C190), a first portion (C191*a*), a second portion (C191*b*), a third portion (C191*c*), a fourth portion (C191*d*), and a fifth portion (C191*e*). Inner boundary (C189) defines the innermost portion of first planar surface (C184*a*). Outer boundary (C189) defines the outermost portion of first planar surface (C184*a*). Inner boundary (C189) is stepped relative to outer boundary (C190). Inner boundary (C189) includes first, second, third, and fourth inner walls (C194*a-d*). First inner wall (C194*a*) and third inner wall (C194*c*) extend parallel to first and second lateral sides (C170, C172). Second inner wall (C194*b*) partially defines first inwardly facing projection (C174*a*) together with first inner wall (C194*a*). As shown, second inner wall (C194*b*) extends perpendicular to first inner wall (C194*a*) and first lateral side (C170). Third inner wall (C194*c*) extends parallel to first and second lateral side (C170). Second inner wall (C194*b*) partially defines first inwardly facing projection (C174*a*) together with first inner wall (C194*a*). As shown, second inner wall (C194*b*) extends perpendicular to first inner wall (C194*a*) and first lateral side (C170).

First portion (C191*a*) defines a first distance (d1) between inner and outer boundaries (C189, C190) in a direction perpendicular to outer boundary (C190). Second portion (C191*b*) includes first inwardly facing projection (C174*a*). Second portion (C191*b*) defines a second distance (d2) between the inner and outer boundaries (C189, C190) in the direction perpendicular to the outer boundary (C190). Second distance (d2) is greater than first distance (d1). As shown, second distance (d2) is at least about double first distance (d1). Third portion (C191*c*) defines a third distance (d3) between inner and outer boundaries (C189, C190) in the direction perpendicular to outer boundary (C190). Fourth portion (C191*d*) defines a fourth distance (d4) between the inner and outer boundaries (C189, C190) in the direction perpendicular to the outer boundary (C190). Fourth portion (C191*d*) includes second inwardly facing projection (C174*b*). Fourth distance (d4) is greater than third distance (d3). Fifth portion (C191*e*) defines a first distance (d5) between inner and outer boundaries (C189, C190) in a direction perpendicular to outer boundary (C190). As shown, first distance (d1) is equal to third distance (d3) and fifth distance (d5). Similarly, fourth distance (d4) is equal to second distance (d2). First, third, and fifth portions (C191*a*, C191*c*, C191*e*) each define generally rectangular shapes. Second and fourth portions (C191*b*, C191*d*) each define generally triangular shapes. As shown, without the inclusion of first and second inwardly facing projection (C174*a-b*), area (A1) would be substantially uniform along first end portion (C176).

Second end portion (C178) is a mirror image of first end portion (C176). Second end portion (C178) is tapered inwardly towards the second longitudinal end (C168) such that the second end portion (C178) is narrower at the second longitudinal end (C168) than at the first and second lateral sides (C170, C172) of the cartridge pocket (C168). More specifically, the portions of the second end portion (C178) that extend from the first and second lateral sides (C170, C172) towards the second longitudinal end (C168) provide a substantially frustoconical shape for the second end portion (C178) at the second longitudinal end (C168) Second end portion (C178) includes a third inwardly facing projection (C174*c*), a fourth inwardly facing projection (C174*d*), and second planar surface (C184*b*). Third inwardly facing projection (C174*c*) is similar to first inwardly facing projection (C174*a*), and fourth inwardly facing projection (C174*d*) is similar to second inwardly facing projection (C174*b*). Third and fourth inwardly facing projections (C174*c-d*) extend away from second end portion (C178) inwardly toward first end portion (C176). Third inwardly facing projection (C174*c*) extends inwardly between second longitudinal end (C168) and first lateral side (C170). Third inwardly facing projection (C174*c*) extends toward first longitudinal end (C166) and second lateral side (C172) of cartridge pocket (C128). Fourth inwardly facing projection (C174*d*) extends inwardly between second longitudinal end (C168) and second lateral side (C172). Fourth inwardly facing projection (C174*d*) extends toward first longitudinal end (C166) and first lateral side (C170).

Second planar surface (C184*b*) wraps around second longitudinal end (C168) of cartridge pocket (C128). Second planar surface (C184*b*) defines a maximum height (hep) of engagement protrusion (C130*a-f*) relative to deck (C124). Second planar surface (C184*b*) extends substantially parallel to deck 124). Second planar surface (C184*b*) is partially defined by third inwardly facing projection (C174*c*). Second planar surface (C184*b*) has a non-uniform area (A2) defined at least in part by third inwardly facing projection (C174*c*). As shown, second planar surface (C184*b*) has a non-uniform area (A) due to third and fourth and second inwardly facing projections (C174*c-d*). Second planar surface (C184*b*) includes an inner boundary (C195), an outer boundary (C196), a first portion (C197*a*), a second portion (C197*b*), a third portion (C197*c*), a fourth portion (C197*d*), and a fifth portion (C197*c*). Inner boundary (C195) defines the innermost portion of second planar surface (C184*b*). Outer boundary (C195) defines the outermost portion of second planar surface (C184*b*). Inner boundary (C195) is stepped relative to outer boundary (C196). Inner boundary (C195) includes first and second inner walls (C198*a-b*). First inner wall (C198*a*) partially defines third inwardly facing projection (C174*c*). First inner wall (C198*a*) extends parallel to first lateral side (C170). Second inner wall (C198*b*) partially defines third inwardly facing projection (C174*c*) together with first inner wall (C198*a*). As shown, second inner wall (C198*b*) extends perpendicular to first inner wall (C198*a*) and first lateral side (C170).

Similar to first planar surface (C184*a*), first portion (C197*a*) of second planar surface (C184*b*) defines first distance (d1), second portion (C197*b*) defines second distance (d2), third portion (C197*c*) defines third distance (d3), fourth portion (C197*d*) defines fourth distance (d4), and fifth portion (C197*e*) defines a first distance (d5). First, second, third, fourth, and fifth distances (d1-d5) are measured between the inner and outer boundaries (C195, 196) in the direction perpendicular to the outer boundary (C196). Similar to second portion (C191*b*), second portion (C197*b*) includes third inwardly facing projection (C174*c*). Similar to fourth portion (C191*d*), fourth portion (C197*d*) includes fourth inwardly facing projection (C174*d*). First, third, and fifth portions (C197*a*, C197*c*, C197*e*) each define generally rectangular shapes. Second and fourth portions (C197*b*, C197*d*) each define generally triangular shapes. As shown, without the inclusion of third and fourth inwardly facing projections (C174*c-d*), area (A2) of second planar surface (C184*b*) would be substantially uniform.

Inwardly facing projections (C174*a-d*) increase the cross-sectional area of planar surfaces (C184*a-b*). Inwardly facing projections (C174*a-d*) increase the surface area configured contact tissue (T) and/or buttress (C188). For example, by increasing the cross-sectional area of planar surfaces (C184*a-b*), inwardly facing projections (C174*a-d*) may increase the adhesion of buttress (C188) (see FIGS. 16-17) to engagement protrusions (C130*a-f*) and/or prevent movement of tissue (T) during firing. Inwardly facing projections (C174*a-d*) increase the area (A1, A2) which may encourage release of buttress (C188) and/or tissue (T) from engagement protrusions (C130*a-f*) after contacting tissue (T).

The shaded surfaces of FIG. 13 depict planar surfaces (C184*a-c*) of engagement protrusion (C130*d*) and adjacent interconnections (C160). Planar surfaces (C184*a-e*) are substantially parallel to deck (C124). Planar surfaces (C184*a-b*) are generally U-shaped with an increased area due to inwardly facing projections (C174). Planar surface (C184*c*) is formed by interconnection (C160) and first end portion (C176). Planar surface (C184*d*) is formed by interconnection (C160) and second end portion (C178). Planar surface (C184*e*) is formed between second lateral side (C172) of cartridge pocket (C128) and lateral portion (C180) of engagement protrusion (C130*d*). Planar surfaces (C184*c-e*) are substantially rectangular.

With continued reference to FIG. 13, engagement protrusion (C130*d*) has a maximum width (Wep) in the direction transverse to longitudinal axis (LA). Interconnection (C160) has a maximum width (Wi) in the direction transverse to longitudinal axis (LA). Maximum width (Wp) of engagement protrusion (C130*d*) is greater than maximum width (Wi) of interconnection (C160). Cartridge pocket (C128) has a maximum width (Wc) defined by a distance between first and second lateral sides (C170, C172) of cartridge pocket (C128) in the direction transverse to longitudinal axis (LA). Maximum width (Wc) of cartridge pocket (C128) is greater than maximum width (Wi) of interconnection (C160). First and second end portions (C176, C178) have a maximum width (Wep) in the direction transverse to longitudinal axis (LA) that is greater than maximum width (Wi) of interconnection (C160).

Figure 14:
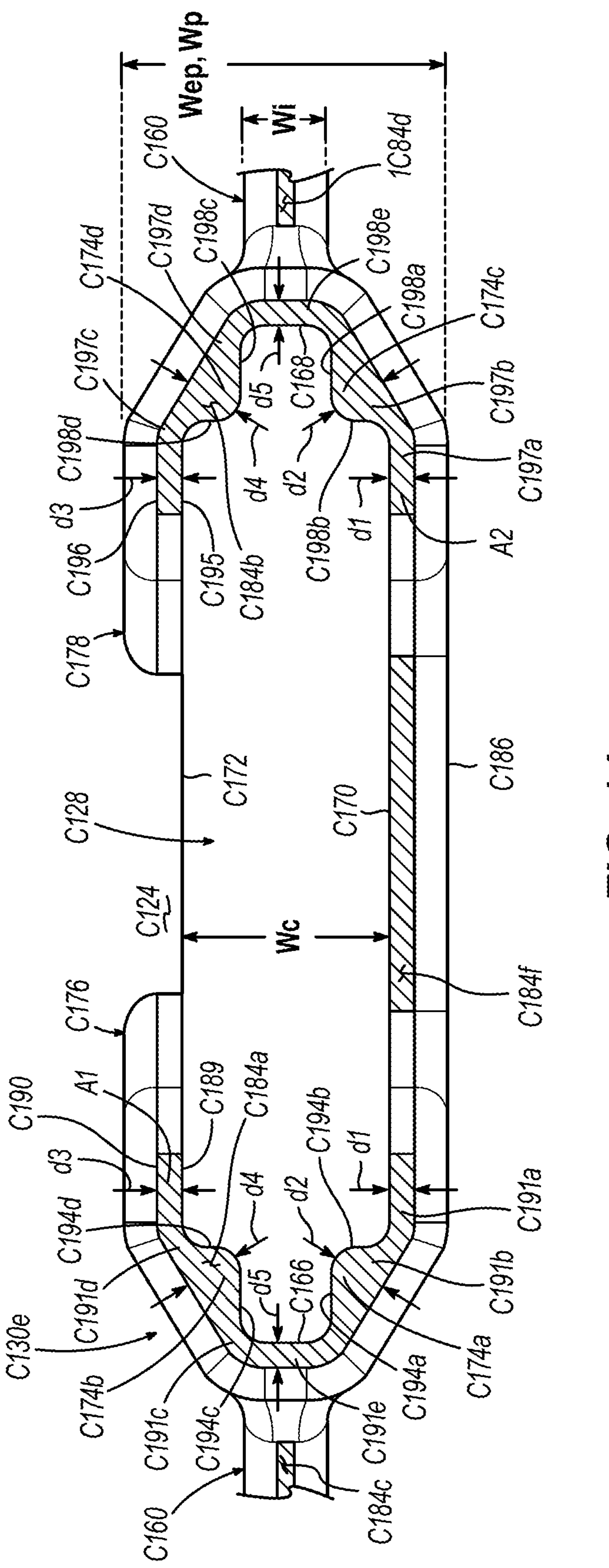
FIG. 14 depicts an enlarged top view of another engagement protrusion and accompanying interconnections partially surrounding a cartridge pocket of the cartridge body of FIG. 12.

FIG. 14 shows an enlarged top view of cartridge pocket (C128), engagement protrusion (C130*e*), and adjacent interconnections (C160) of inner rows (C150) of FIGS. 9 and 12. Engagement protrusion (C130*e*) is a mirror image of engagement protrusion (C130*d*). Similar to engagement protrusion (C130*d*) includes a first end portion (C176) and a second end portion (C178). Unlike engagement protrusion (C130*d*) where lateral portion (C180) extends longitudinally along second lateral side (C172), lateral portion (C186) extends longitudinally along first lateral side (C170) of cartridge pocket (C128). Engagement protrusion (C130*c*) does not extend along second lateral side (C172) of cartridge pocket (C128) such that second lateral side (C172) opens directly to deck (C124). Similar to lateral portion (C180), lateral portion (C186) extends continuously between first and second end portions (C176, C178) of engagement protrusion (C130*c*). Engagement protrusion (C130*e*) and adjacent interconnections (C160) includes planar surfaces (C184*a-d*). Engagement protrusion (C130*e*) includes planar surface (C184*f*) instead of planar surface (C184*c*). Planar surface (C184*f*) is formed between first lateral side (C170) of cartridge pocket (C128) and lateral portion (C186) of engagement protrusion (C130*e*). Planar surface (C184*f*) is substantially rectangular.

Figure 15:
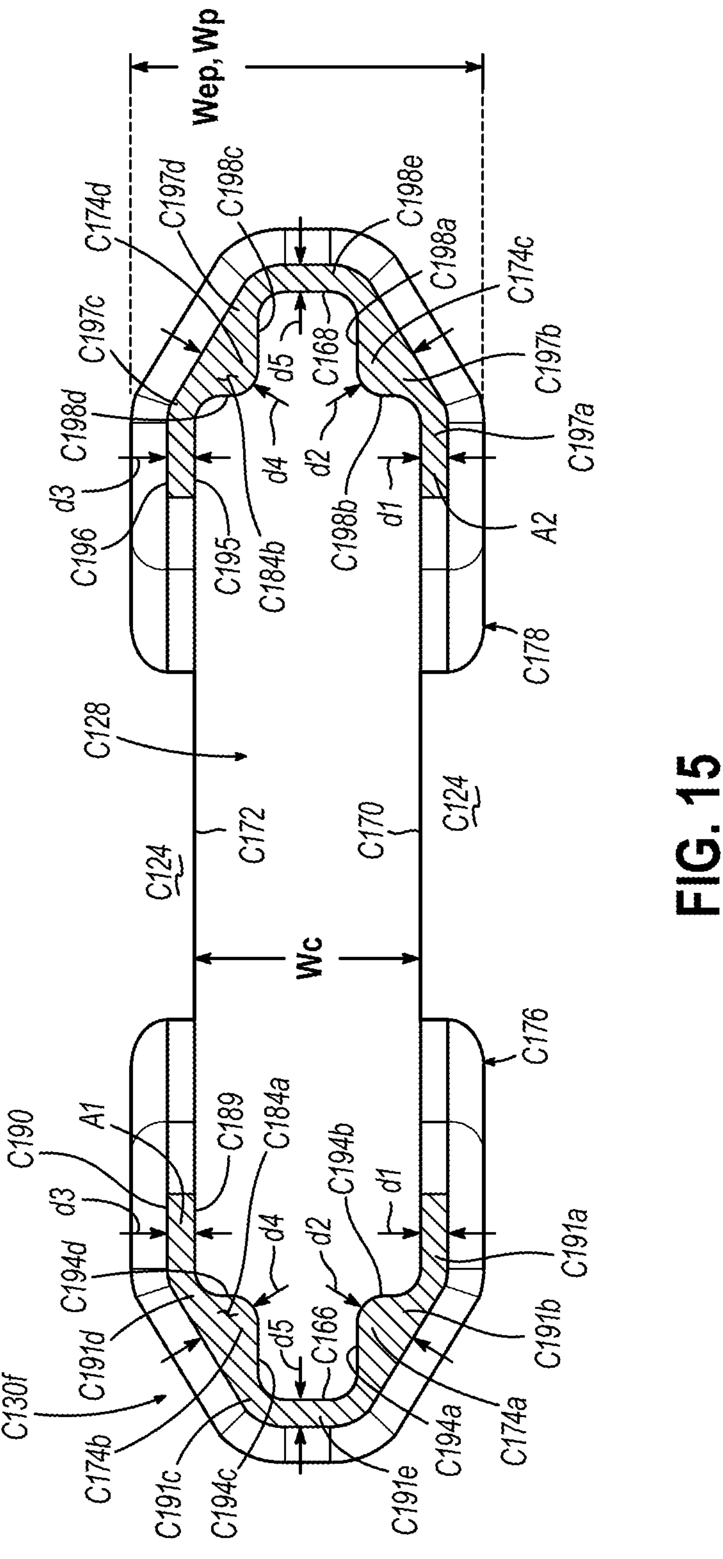
FIG. 15 depicts an enlarged top view of another engagement protrusion partially surrounding a cartridge pocket of the cartridge body of FIG. 12.

FIG. 15 shows an enlarged top view of cartridge pocket (C128) and engagement protrusion (C130*f*) of middle and outer rows (C152, C154) of FIG. 12. Similar to engagement protrusions (C130*d-e*), engagement protrusion (C130*f*) includes a first end portion (C176) and a second end portion (C178). Unlike engagement protrusions (C130*d-c*), engagement protrusion (C130*f*) does not include a lateral portion (e.g., lateral portions (C180, C186)). Instead, both first and second lateral sides (C170, C172) of cartridge pocket (C128) open directly to deck (C124). First and second end portions (C176) are not linked together above deck (C124). Additionally, engagement protrusion (C130*f*) is not linked with another engagement protrusion (C130*a-f*) using interconnections (C160).

Similar to engagement protrusion (C130*d*), first end portion (C176) of engagement protrusions (C130*d*, C130*f*) of FIGS. 14 and 15 includes first inwardly facing projection (C174*a*), second inwardly facing projection (C174*b*), and first planar surface (C184*a*). Similar to engagement protrusion (C130*d*), second end portion (C178) of engagement protrusions (C130*d*, C130*f*) includes third inwardly facing projection (C174*c*), fourth inwardly facing projection (C174*d*), and second planar surface (C184*d*). First planar surface (C184*a*) includes inner boundary (C189), outer boundary (C190), first portion (C191*a*), second portion (C191*b*), third portion (C191*c*), fourth portion (C191*d*), and fifth portion (C191*e*). Second planar surface (C184*b*) includes inner boundary (C195), outer boundary (C196), first portion (C197*a*), second portion (C197*b*), third portion (C197*c*), fourth portion (C197*d*), and fifth portion (C197*e*). These features are shown and described above with reference to FIG. 13. While FIGS. 13-15 show engagement protrusions (C130*d-f*), certain aspects also apply to engagement protrusions (C130*a-c*) shown and described above with reference to FIGS. 9 and 12. For example, engagement protrusions (C130*a-c*) each include a second end portion similar to second end portion (C178). Engagement protrusions (C130*a-c*) respectively include planar surfaces (C158*a-c*) instead of first planar surface (C184*a*). Planar surfaces (C158*a-c*) include inwardly facing projections similar to first and second inwardly facing projections (C174*a-b*).

Figures 16, 17:
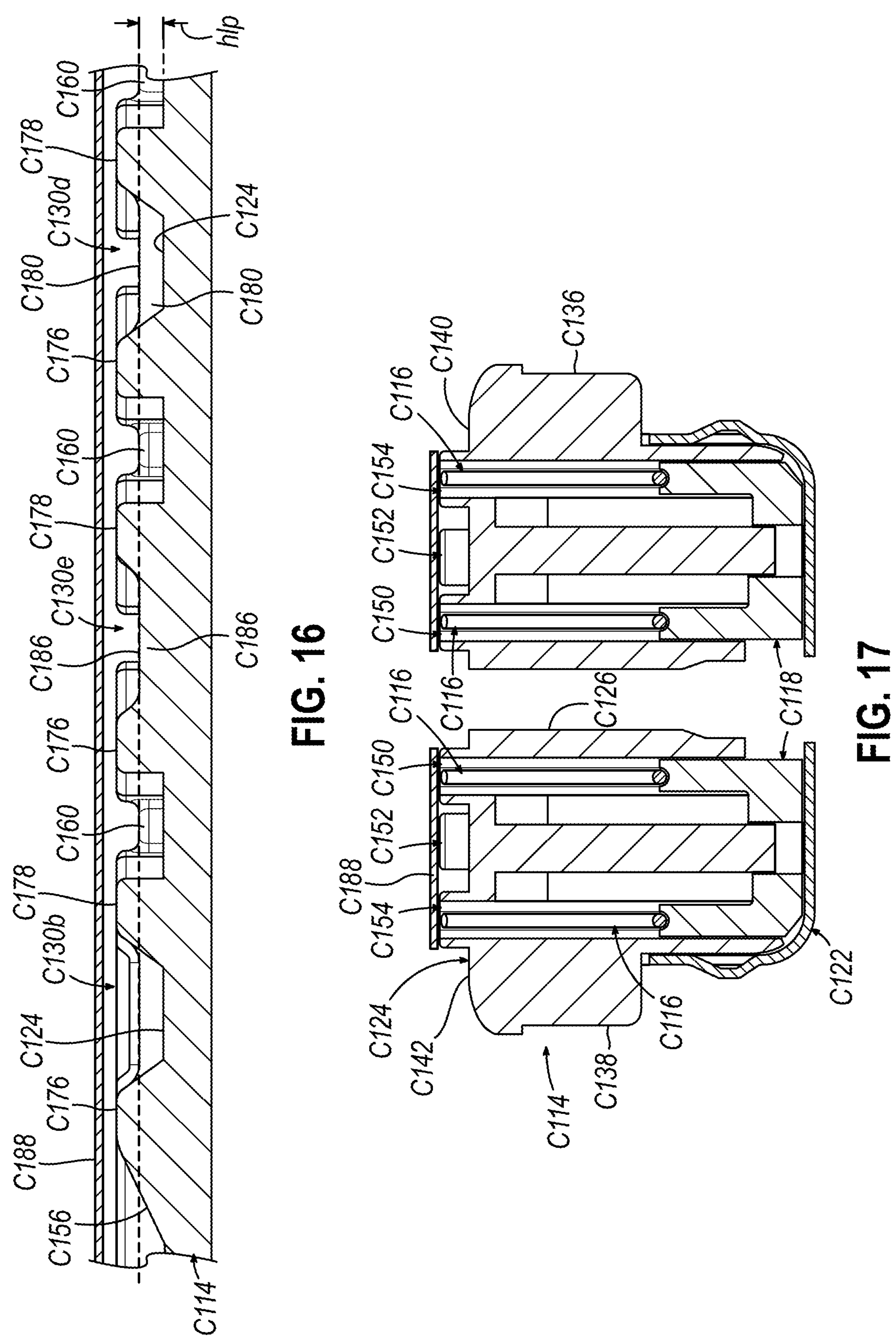
FIG. 16 depicts a partial sectional view of the cartridge body of FIG. 12 taken along line 16-16 of FIG. 12 prior to adhesion of a buttress onto the engagement protrusions of the cartridge body FIG. 12.
FIG. 17 depicts a partial sectional view of the staple cartridge of FIG. 7 after adhesion of the buttress of FIG. 16 onto the engagement protrusions.

FIG. 16 shows a partial sectional view of cartridge body (C114) of FIG. 12 taken along line 16-16 prior to adhesion of a buttress (C188) onto engagement protrusions (C130*a-f*) of FIG. 12. As shown, lateral portions (C180, C186) connect first and second end portions (C176, C178). Lateral portions (C180, C186) alternate between adjacent cartridge pockets (C128) along an entire length of inner row (C144). Considering first row (C150) on second deck side (C140), lateral portions (C180, C186) alternate from first lateral side (C170) (e.g., side adjacent to elongate slot (C126)) to second lateral side (C172) (e.g., side opposite to elongate slot (C126)) moving proximally along elongate slot (C126). Alternating lateral portions (C180, C186) on inner row (C144) of cartridge pockets (C128) may influence tissue retainment during clamping and firing.

FIG. 17 shows a partial sectional view of staple cartridge (C110) of FIG. 7 after adhesion of buttress (C188) onto engagement protrusions (C130*a-f*). In some instances, it may be desirable to equip end effector (40) of surgical stapler (10) with an adjunct material, such as a buttress, to reinforce the mechanical fastening of tissue (T) provided by staples (C86). In addition to or as an alternative to providing structural support and integrity to a line of staples (C86), a buttress (C188) may provide various other kinds of effects such as spacing or gap-filling, administration of therapeutic agents, and/or other effects. In some instances, a buttress may be provided on engagement protrusions (C130*d-e*). As described above, deck (C124) houses staples (C116), which are driven by staple driver (C118). In some other instances, buttress (C188) may be provided on the surface of an anvil (e.g., anvil (44)) that faces staple cartridge (C110). It should also be understood that a first buttress (C188) may be provided on deck (C124) and a second buttress (not shown) but similar to buttress (C188) is provided on anvil (44) of the same end effector. Exemplary buttress assemblies, exemplary materials and techniques for applying buttress assemblies, and exemplary buttress applier cartridges may be configured in accordance with at least some of the teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and/or U.S. Pat. No. 11,166,724, entitled "Adhesive Distribution on Buttress for Surgical Stapler," issued Nov. 9, 2021, the disclosures of which are incorporated by reference herein. Increased contact area of planar surfaces (C158*a-c*, C184*a-f*) may affect adhesion of buttress (C188) to engagement protrusions (C130*a-f*). While planar surfaces (C158*a-c*, C184*a-f*) were the upper most surfaces configured to contact buttress (C188), it is also envisioned that lateral portions (C180, C186) and/or protrusions (C160) may contact buttress (C188).

Figure 18:
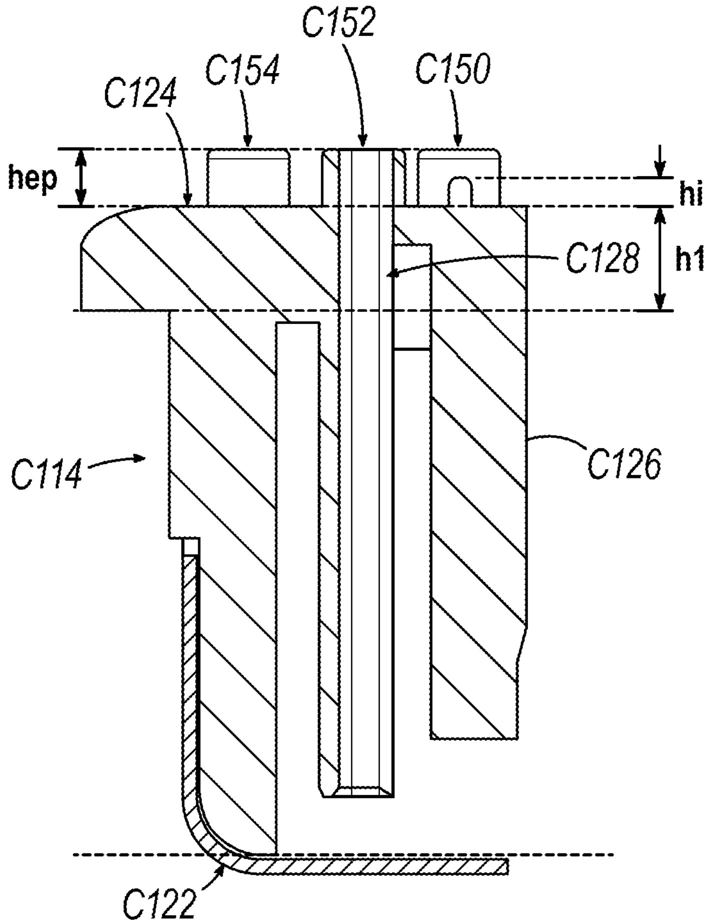
FIG. 18 depicts a partial sectional view of the staple cartridge of FIG. 17 but taken along a different portion.

FIG. 18 shows a partial sectional view of cartridge body (C114) taken along a different portion than FIG. 17. As shown, each engagement protrusion (C130*a-f*) has the same height (e.g., extends away from deck (C124) the same distance). Particularly, first and second end portions (C176, C178) of engagement protrusions (C130*a-f*) extend from deck (C124) a maximum height (hep). As shown, maximum height (hep) is about 0.020 inches (0.508 millimeters). Increasing maximum height (hep) accommodates thicker tissue (T). While first and second end portions (C176, C178) are shown as extending from deck (C124) the same maximum height (hep), first end portion (C176) may extend from deck (C124) a greater or lesser amount than second end portion (C178). Lateral portions (C180, C186) of engagement protrusions (C130*d-e*) extend from deck (C124) a maximum height (hlp) (see FIG. 16). Interconnection (C160) extends from deck (C124) a maximum height (hi). As shown, maximum height (hep) of first and second end portions (C176, C178) is greater than maximum height (hi) of interconnection. In other words, maximum height (hi) of interconnections (C160) and maximum height of (hlp) of lateral portions (C180, C186) are each less than maximum height (hep) of first and second end portions (C176, C178). For example, maximum height (hi) of interconnections (C160) and maximum height of (hlp) of lateral portions (C180, C186) may be each about half of maximum height (hep) of first and second end portions (C176, C178). Deck (C124) is planar between engagement protrusions (C130*a-c*) to proximal end (C132) of cartridge body (C114). Height (h1) is about 0.037 inches (0.9398 millimeters).

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus (C110) comprising: (a) a cartridge body (C114); (b) a deck (C124) defined by the cartridge body (C114), wherein the deck (C124) is configured to compress tissue (T) against an anvil (C44) of a surgical stapler (C10); (c) an elongate slot (C126) formed in the deck (C124); (d) a plurality of pockets (C128) formed in the deck (C124) and configured to house a plurality of staples (C116), wherein the plurality of pockets (C128) includes a first pocket (C128), the first pocket (C128) comprising: (i) a first longitudinal end (C166), (ii) a second longitudinal end (C168) disposed opposite the first longitudinal end (C166, C168), (iii) a first lateral side (C170) disposed between the first and second longitudinal ends (C166, C168), and (iv) a second lateral side (C172) disposed between the first and second longitudinal ends (C166, C168) and opposite to the first lateral side (C170); and (e) a plurality of engagement protrusions (C130*a-f*) extending from the deck (C124) and configured to grip tissue (T) or an adjunct material (C188), wherein the plurality of engagement protrusions (C130*a-f*)

includes a first engagement protrusion (C130*a-f*) associated with the first pocket (C128) and that includes a first end portion (C176) that tapers inwardly towards the first longitudinal end (C168) such that the first end portion (C176) is narrower at the longitudinal end (C168) than at first and second lateral sides (C170, C172) of the first pocket (C128), the first engagement protrusion (C130*a-f*) comprising: (i) a first inwardly facing projection (C174*a*) that extends inwardly between the first longitudinal end (C166) and the first lateral side (C170) of the first pocket (C128), and (ii) a first planar surface (C184*a*) extending substantially parallel to the deck (C124), wherein the first planar surface (C184*a*) is defined by the first inwardly facing projection (C174*a*), wherein the first planar surface (C184*a*) defines a maximum height (hp) of the engagement protrusion (C130*a-f*) relative to the deck (C124), wherein the first planar surface (C184*a*) has a non-uniform area (A1) defined at least in part by the first inwardly facing projection (C174*a*).

Example 2

The apparatus (C110) of Example 1, the first planar surface (C184*a*) comprising: (A) an inner boundary (C189), (B) an outer boundary (C190), (C) a first portion (C191*a*) defining a first distance (d1) between the inner and outer boundaries (C189, C190) in a direction perpendicular to the outer boundary (C190), and (D) a second portion (C191*b*) that includes the first inwardly facing projection (C174*a*), wherein the second portion (C191*b*) defines a second distance (d2) between the inner and outer boundaries (C189, C190) in the direction perpendicular to the outer boundary (C190), wherein the second distance (d2) is greater than the first distance (d1).

Example 3

The apparatus (C110) of Example 2, wherein the second distance (d2) is at least about double the first distance (d1).

Example 4

The apparatus (C110) of any of Examples 2 through 3, wherein the inner boundary (C189) is stepped relative to the outer boundary (C190).

Example 5

The apparatus (C110) of any of Examples 2 through 4, wherein the inner boundary (C189) includes a first inner wall (C194*a*) that partially defines the first inwardly facing projection (C174*a*), wherein the first inner wall (C194*a*) extends substantially parallel to the first lateral side (C170).

Example 6

The apparatus of Example 5, wherein the inner boundary (C189) includes a second inner wall (C194*b*) that partially defines the first inwardly facing projection (C174*a*) together with the first inner wall (C194*a*), wherein the second inner wall (C194*b*) extends substantially perpendicular to the first inner wall (C194*a*).

Example 7

The apparatus (C110) of any of Examples 1 through 6, wherein the first inwardly facing projection (C174*a*) extends toward the second longitudinal end (C168) and the second lateral side (C172).

Example 8

The apparatus (C110) of any of Examples 1 through 7, wherein the first planar surface (C184*a*) wraps around the first longitudinal end (C166) of the first pocket (C128).

Example 9

The apparatus (C110) of any of Examples 1 through 8, wherein the first engagement protrusion (C130*a-f*) includes a first end portion (C176) that wraps around the first longitudinal end (C166) of the first pocket (C128), the first end portion (C176) comprising: (i) the first inwardly facing projection (C174*a*), (ii) a second inwardly facing projection (C174*b*) that extends inwardly between the first longitudinal end (C166) and the second lateral sides (C170, C172), and (iii) the first planar surface (C184*a*) that extends substantially parallel to the deck (C124), wherein the first planar surface (C184*a*) has a non-uniform area (A1) defined at least in part by the first and second inwardly facing projections (C174*a-b*).

Example 10

The apparatus (C110) of Example 9, wherein the second inwardly facing projection (C174*b*) extends toward the second longitudinal end (C168) and the first lateral side (C170).

Example 11

The apparatus (C110) of any of Examples 1 through 8, further comprising: (i) a second inwardly facing projection (C174*c*) that extends inwardly between the second longitudinal end (C170) and the second lateral side (C172), and (ii) a second planar surface (C184*b*) extending substantially parallel to the deck (C124), wherein the first and second planar surfaces (C184*a-b*) define the maximum height (hp) of the engagement protrusion (C130*a-f*) relative to the deck (C124), wherein the second planar surface (C184*b*) has a non-uniform area (A2) defined at least in part by the second inwardly facing projection (C174*c*).

Example 12

The apparatus (C110) of any of Examples 1 through 10, wherein the first and second lateral sides (C170, C172) extend substantially parallel to the elongate slot (C126).

Example 13

The apparatus (C110) of any of Examples 1 through 11, wherein the deck (C124) is substantially planar.

Example 14

The apparatus (C110) of any of Examples 1 through 12, wherein the first engagement protrusion (C130*a-f*) at least partially surrounds the first pocket (C128).

Example 15

The apparatus (C110) of Example 14, wherein the lateral portion (C186) of the first engagement protrusion (C130*a-f*) extends on the first lateral side (C170) of the first pocket (C128), wherein the first engagement protrusion (C130*a-f*) does not extend longitudinally along the second lateral side (C172) of the first pocket (C128) such that the second lateral side (C172) opens directly to the deck (C124).

The following clauses also relate to various non-exhaustive ways in which the teachings herein may be combined or applied.

1. An apparatus comprising:
   (a) a cartridge body;
   (b) a deck defined by the cartridge body, wherein the deck is configured to compress tissue against an anvil of a surgical stapler;
   (c) an elongate slot formed in the deck;
   (d) a plurality of pockets formed in the deck and configured to house a plurality of staples, wherein the plurality of pockets includes a first pocket, the first pocket comprising:
      (i) a first longitudinal end,
      (ii) a second longitudinal end disposed opposite the first longitudinal end,
      (iii) a first lateral side disposed between the first and second longitudinal ends, and
      (iv) a second lateral side disposed between the first and second longitudinal ends and opposite to the first lateral side; and
   (e) a plurality of engagement protrusions extending from the deck and configured to grip tissue or an adjunct material, wherein the plurality of engagement protrusions includes a first engagement protrusion associated with the first pocket and that includes a first end portion that tapers inwardly towards the first longitudinal end such that the first end portion is narrower at the longitudinal end than at the first and second lateral sides of the first pocket, the first engagement protrusion comprising:
      (i) a first inwardly facing projection that extends inwardly between the first longitudinal end and the first lateral side of the first pocket, and
      (ii) a first planar surface extending substantially parallel to the deck, wherein the first planar surface is defined by the first inwardly facing projection, wherein the first planar surface defines a maximum height of the first engagement protrusion relative to the deck, wherein the first planar surface has a non-uniform area defined at least in part by the first inwardly facing projection.
2. The apparatus of Clause 1, the first planar surface comprising:
   (A) an inner boundary,
   (B) an outer boundary,
   (C) a first portion defining a first distance between the inner and outer boundaries in a direction perpendicular to the outer boundary, and
   (D) a second portion that includes the first inwardly facing projection, wherein the second portion defines a second distance between the inner and outer boundaries in the direction perpendicular to the outer boundary, wherein the second distance is greater than the first distance.
3. The apparatus of Clause 2, wherein the second distance is at least about double the first distance.
4. The apparatus of Clause 2, wherein the inner boundary is stepped relative to the outer boundary.
5. The apparatus of Clause 2, wherein the inner boundary includes a first inner wall that partially defines the first inwardly facing projection, wherein the first inner wall extends substantially parallel to the first lateral side.
6. The apparatus of Clause 5, wherein the inner boundary includes a second inner wall that partially defines the first inwardly facing projection together with the first inner wall, wherein the second inner wall extend extends substantially perpendicular to the first inner wall.
7. The apparatus of Clause 1, wherein the first inwardly facing projection extends toward the second longitudinal end and the second lateral side.
8. The apparatus of Clause 1, wherein the first planar surface wraps around the first longitudinal end of the first pocket.
9. The apparatus of Clause 1, wherein the first engagement protrusion includes a first end portion that wraps around the first longitudinal end of the first pocket, the first end portion comprising:
   (i) the first inwardly facing projection,
   (ii) a second inwardly facing projection that extends inwardly between the first longitudinal end and the second lateral, and
   (iii) the first planar surface that extends substantially parallel to the deck, wherein the first planar surface has a non-uniform area defined at least in part by the first and second inwardly facing projections.
10. The apparatus of Clause 9, wherein the second inwardly facing projection extends toward the second longitudinal end and the first lateral side.
11. The apparatus of Clause 1, further comprising:
   (i) a second inwardly facing projection that extends inwardly between the second longitudinal end and the second lateral side, and
   (ii) a second planar surface extending substantially parallel to the deck, wherein the first and second planar surfaces define the maximum height of the engagement protrusion relative to the deck, wherein the second planar surface has a non-uniform area defined at least in part by the second inwardly facing projection.
12. The apparatus of Clause 1, wherein the first and second lateral sides extend substantially parallel to the elongate slot.
13. The apparatus of Clause 1, wherein the deck is substantially planar.
14. The apparatus Clause 1, wherein the first engagement protrusion at least partially surrounds the first pocket.
15. The apparatus of Clause 14, wherein the lateral portion of the first engagement protrusion extends on the first lateral side of the first pocket, wherein the first engagement protrusion does not extend longitudinally along the second lateral side of the first pocket such that the second lateral side opens directly to the deck.
16. An apparatus comprising:
   (a) a cartridge body;
   (b) a deck defined by the cartridge body, wherein the deck is configured to compress tissue against an anvil of a surgical stapler;
   (c) an elongate slot formed in the deck;
   (d) a plurality of pockets formed in the deck and configured to house a plurality of staples, wherein the plurality of pockets includes a first pocket; and
   (e) a plurality of engagement protrusions extending from the deck and configured to grip tissue or an adjunct material, wherein the plurality of engagement protrusions includes a first engagement protrusion associated with the first pocket and that includes a first end portion that tapers inwardly towards the first longitudinal end such that the first end portion is narrower at the longitudinal end than at first and second lateral sides of the first pocket, the first engagement protrusion comprising:

(i) a first inwardly facing projection, and (ii) a first planar surface extending substantially parallel to the deck, wherein the first planar surface defines a maximum height of the first engagement protrusion relative to the deck, the first planar surface comprising:

(A) an inner boundary, (B) an outer boundary, (C) a first portion defining a first distance between the inner and outer boundaries in a direction perpendicular to the outer boundary, and (D) a second portion that includes the first inwardly facing projection, wherein the second portion defines a second distance between the inner and outer boundaries in the direction perpendicular to the outer boundary, wherein the second distance is greater than the first distance.

17. The apparatus of Clause 16, wherein the inner boundary includes a first inner wall that partially defines the first inwardly facing projection, wherein the first inner wall extends parallel to the first lateral side.

18. An apparatus comprising:

(a) a cartridge body;

(b) a deck defined by the cartridge body, wherein the deck is configured to compress tissue against an anvil of a surgical stapler;

(c) an elongate slot formed in the deck;

(d) a plurality of pockets formed in the deck and configured to house a plurality of staples, wherein the plurality of pockets includes a first pocket; and (e) a plurality of engagement protrusions extending from the deck and configured to grip tissue or an adjunct material, wherein the plurality of engagement protrusions includes a first engagement protrusion associated with the first pocket and that includes a first end portion that tapers inwardly towards the first longitudinal end such that the first end portion is narrower at the longitudinal end than at first and second lateral sides of the first pocket, the first engagement protrusion comprising:

(i) a first inwardly facing projection that extends inwardly toward the cartridge pocket, (ii) a second inwardly facing projection that extends inwardly toward the cartridge pocket, and (iii) a first planar surface extending substantially parallel to the deck, wherein the first planar surface defines a maximum height of the first engagement protrusion relative to the deck, wherein the first planar surface has a non-uniform area defined at least in part by the first and second inwardly facing projections.

19. The apparatus of Clause 18, the first planar surface comprising:

(A) an inner boundary, (B) an outer boundary, (C) a first portion defining a first distance between the inner and outer boundaries in a direction perpendicular to the outer boundary, and (D) a second portion that includes the first inwardly facing projection, wherein the second portion defines a second distance between the inner and outer boundaries in the direction perpendicular to the outer boundary, wherein the second distance is greater than the first distance.

20. The apparatus of Clause 19, wherein the first planar surface further comprises a third portion, wherein the third portion defines a third distance between perpendicular to the outer boundary, wherein the second distance is greater than the first distance, wherein the third distance is greater than either of the first and second distances.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 18/588,147, "Surgical Stapler Cartridge Having Intermediate Raised Tissue Engagement Protrusions," filed on Feb. 27,2024, issied as U.S. Pat. No. 12,246,880 on Sep. 30, 2025, U.S. patent application Ser. No. 18/588,206, entitled "Surgical Stapler Cartridge Having Raised Surface to Promote Buttress Adhesion," filed on Feb. 27, 2024, issued as U.S. Pat. No. 12,390,220 on Aug. 19, 2025; U.S. patent application Ser. No. 18/588,240, entitled "Surgical Stapler Cartridge Having Cartridge Retention Features," filed on Feb. 27, 2024, issued as U.S. Pat. No. 12,285,170 on Apr. 29, 2025; U.S. patent application Ser. No. 18/588,269, entitled "Incompatible Staple Cartridge Use Prevention Features for Surgical Stapler," filed on Feb. 27, 2024, issued as U.S. Pat. No. 12,414,771 on Sep. 16, 2025; U.S. patent application Ser. No. 18/588,684, entitled "Method of Surgical Stapling" filed on Feb. 27, 2024, issued as U.S. Pat. No. 12,471,913 on Nov. 18, 2025; and/or U.S. patent application Ser. No. 18/588,094, entitled "Incompatible Staple Cartridge Use Prevention Features for Surgical Stapler," filed on Feb. 27, 2024, issued as U.S. Pat. No. 12,324,583 on Jun. 10, 2025. In addition, or alternatively, any one or more of the teachings herein may be combined with any one or more of the teachings disclosed in U.S. Pat. App. No. 63/459,739, entitled "Surgical Stapler Anvil Having Staple Forming Pockets with Laterally Varying Orientations," filed on Apr. 17, 2023, now expired. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:

(a) a cartridge body;

(b) a deck defined by the cartridge body, wherein the deck is configured to compress tissue against an anvil of a surgical stapler;

(c) an elongate slot formed in the deck;

(d) a plurality of pockets formed in the deck and configured to house a plurality of staples, wherein the plurality of pockets includes a first pocket, wherein the deck extends to the first pocket, the first pocket comprising:

(i) a first longitudinal end, (ii) a second longitudinal end disposed opposite the first longitudinal end, (iii) a first lateral side disposed between the first and second longitudinal ends, and (iv) a second lateral side disposed between the first and second longitudinal ends and opposite to the first lateral side; and (e) a plurality of engagement protrusions extending from the deck and configured to grip tissue or an adjunct material, wherein the plurality of engagement protrusions includes a first engagement protrusion associated with the first pocket and that includes a first end portion that tapers inwardly towards the first longitudinal end such that the first end portion is narrower at the first longitudinal end than at the first and second lateral sides of the first pocket, the first engagement protrusion extending from the first longitudinal end to the second longitudinal end, the first engagement protrusion comprising:

(i) a first inwardly facing projection that extends inwardly between the first longitudinal end and the first lateral side of the first pocket, and (ii) a first planar surface extending substantially parallel to the deck, wherein the first planar surface is defined by the first inwardly facing projection, wherein the first planar surface defines a maximum height of the first engagement protrusion relative to the deck, wherein the first planar surface has a non-uniform area defined at least in part by the first inwardly facing projection.

2. The apparatus of claim 1, the first planar surface comprising:

(A) an inner boundary, (B) an outer boundary, (C) a first portion defining a first distance between the inner boundary and the outer boundary in a direction perpendicular to the outer boundary, and (D) a second portion that includes the first inwardly facing projection, wherein the second portion defines a second distance between the inner boundary and the outer boundary in the direction perpendicular to the outer boundary, wherein the second distance is greater than the first distance.

3. The apparatus of claim 2, wherein the second distance is at least about double the first distance.

4. The apparatus of claim 2, wherein the inner boundary is stepped relative to the outer boundary.

5. The apparatus of claim 2, wherein the inner boundary includes a first inner wall that partially defines the first inwardly facing projection, wherein the first inner wall extends substantially parallel to the first lateral side.

6. The apparatus of claim 5, wherein the inner boundary includes a second inner wall that partially defines the first inwardly facing projection together with the first inner wall, wherein the second inner wall extend extends substantially perpendicular to the first inner wall.

7. The apparatus of claim 1, wherein the first inwardly facing projection extends toward the second longitudinal end and the second lateral side.

8. The apparatus of claim 1, wherein the first planar surface wraps around the first longitudinal end of the first pocket.

9. The apparatus of claim 1, wherein the first engagement protrusion includes a first end portion that wraps around the first longitudinal end of the first pocket, the first end portion comprising:

(i) the first inwardly facing projection, (ii) a second inwardly facing projection that extends inwardly between the first longitudinal end and the second lateral side, and (iii) the first planar surface that extends substantially parallel to the deck, wherein the first planar surface has a non-uniform area defined at least in part by the first and second inwardly facing projections.

10. The apparatus of claim 9, wherein the second inwardly facing projection extends toward the second longitudinal end and the first lateral side.

11. The apparatus of claim 1, further comprising:

(i) a second inwardly facing projection that extends inwardly between the second longitudinal end and the second lateral side, and (ii) a second planar surface extending substantially parallel to the deck, wherein the first and second planar surfaces define the maximum height of the engagement protrusion relative to the deck, wherein the second planar surface has a non-uniform area defined at least in part by the second inwardly facing projection.

12. The apparatus of claim 1, wherein the first and second lateral sides extend substantially parallel to the elongate slot.

13. The apparatus of claim 1, wherein the deck is substantially planar.

14. The apparatus of claim 1, wherein the first engagement protrusion at least partially surrounds the first pocket.

15. The apparatus of claim 14, wherein a lateral portion of the first engagement protrusion extends on the first lateral side of the first pocket, wherein the first engagement protrusion does not extend longitudinally along the second lateral side of the first pocket such that the second lateral side opens directly to the deck.

16. An apparatus comprising:

(a) a cartridge body;

(b) a deck defined by the cartridge body, wherein the deck is configured to compress tissue against an anvil of a surgical stapler;

(c) an elongate slot formed in the deck;

(d) a plurality of pockets formed in the deck and configured to house a plurality of staples, wherein the plurality of pockets includes a first pocket having a first longitudinal end; and (e) a plurality of engagement protrusions extending from the deck and configured to grip tissue or an adjunct material, wherein the plurality of engagement protrusions includes a first engagement protrusion associated with the first pocket and that includes a first end portion that tapers inwardly towards the first longitudinal end such that the first end portion is narrower at the first longitudinal end than at first and second lateral sides of the first pocket, the first engagement protrusion comprising:

(i) a first inwardly facing projection, and (ii) a first planar surface extending substantially parallel to the deck, wherein the first planar surface defines a maximum height of the first engagement protrusion relative to the deck, the first planar surface comprising:

(A) an inner boundary, (B) an outer boundary, (C) a first portion defining a first distance between the inner boundary and the outer boundary in a direction perpendicular to the outer boundary, and (D) a second portion that includes the first inwardly facing projection, wherein the second portion defines a second distance between the inner boundary and the outer boundary in a direction perpendicular to a straight portion of the outer boundary, wherein the second distance is greater than the first distance.

17. The apparatus of claim 16, wherein the inner boundary includes a first inner wall that partially defines the first inwardly facing projection, wherein the first inner wall extends parallel to the first lateral side.

18. An apparatus comprising:

(a) a cartridge body;

(b) a deck defined by the cartridge body, wherein the deck is configured to compress tissue against an anvil of a surgical stapler;

(c) an elongate slot formed in the deck;

(d) a plurality of pockets formed in the deck and configured to house a plurality of staples, wherein the plurality of pockets includes a first pocket having a first longitudinal end, a first lateral side, and a second lateral side; and (e) a plurality of engagement protrusions extending from the deck and configured to grip tissue or an adjunct material, wherein the plurality of engagement protrusions includes a first engagement protrusion associated with the first pocket and that includes a first end portion that tapers inwardly towards the first longitudinal end such that the first end portion is narrower at the first longitudinal end than at the first lateral side and the second lateral side of the first pocket, the first engagement protrusion comprising:

(i) a first inwardly facing projection that extends inwardly toward the first pocket, (ii) a second inwardly facing projection that extends inwardly toward the first pocket, and (iii) a first planar surface extending substantially parallel to the deck, wherein the first planar surface defines a maximum height of the first engagement protrusion relative to the deck, wherein the first planar surface has a non-uniform area defined at least in part by the first and second inwardly facing projections, wherein the first planar surface defines a substantially right angle opening away from the first pocket.

19. The apparatus of claim 18, the first planar surface comprising:

(A) an inner boundary, (B) an outer boundary, (C) a first portion defining a first distance between the inner boundary and the outer boundary in a direction perpendicular to the outer boundary, and (D) a second portion that includes the first inwardly facing projection, wherein the second portion defines a second distance between the inner boundary and the outer boundary in the direction perpendicular to the outer boundary, wherein the second distance is greater than the first distance.

20. The apparatus of claim 19, wherein the first planar surface further comprises a third portion, wherein the third portion defines a third distance perpendicular to the outer boundary, wherein the second distance is greater than the first distance, wherein the third distance is greater than either of the first and second distances.

* * * * *